US009072492B2

(12) United States Patent
Arditi et al.

(10) Patent No.: US 9,072,492 B2
(45) Date of Patent: Jul. 7, 2015

(54) QUANTIFICATION ANALYSIS OF IMMOBILIZED CONTRAST AGENT IN MEDICAL IMAGING APPLICATIONS

(75) Inventors: Marcel Arditi, Plan-les-Ouates (CH); Tristan Messager, Plan-les-Ouates (CH); Michel Schneider, Plan-les-Ouates (CH); Peter Frinking, Plan-les-Ouates (CH)

(73) Assignee: BRACCO SUISSE SA, Manno (CH)

( * ) Notice: Subject to any disclaimer, the term of this patent is extended or adjusted under 35 U.S.C. 154(b) by 876 days.

(21) Appl. No.: 12/811,089
(22) PCT Filed: Dec. 23, 2008
(86) PCT No.: PCT/EP2008/068247
§ 371 (c)(1),
(2), (4) Date: Oct. 6, 2010
(87) PCT Pub. No.: WO2009/083557
PCT Pub. Date: Jul. 9, 2009

(65) Prior Publication Data
US 2011/0015522 A1  Jan. 20, 2011

(30) Foreign Application Priority Data
Dec. 28, 2007 (EP) .................................... 07124133

(51) Int. Cl.
A61B 8/14 (2006.01)
A61B 8/08 (2006.01)
G06F 19/12 (2011.01)

(52) U.S. Cl.
CPC . *A61B 8/481* (2013.01); *A61B 8/14* (2013.01); *G06F 19/12* (2013.01); *A61B 8/5223* (2013.01)

(58) Field of Classification Search
None
See application file for complete search history.

(56) References Cited

U.S. PATENT DOCUMENTS 5,203,337 A * 4/1993 Feldman ........................ 600/463
5,287,273 A * 2/1994 Kupfer et al. .................. 600/431

(Continued)

FOREIGN PATENT DOCUMENTS

EP 0458745 11/1991
EP 0554213 8/1993

(Continued)

OTHER PUBLICATIONS

Jonathan R. Lindner, Suad Ismail, William D. Spotnitz, Danny M. Skyba, Ananda R.Jayaweera and Sanjiv Kaul, "Albumin Microbubble Persistence During Myocardial Contrast Echocardiography Is Associated With Microvascular Endothelial Glycocalyx Damage", Circulation 1998;98;2187-2194 by American Heart Association. 7272 Greenville Avenue, Dallas, TX 72514—Print ISSN: 0009-7322. Online ISSN: 1524-4539.
Gregory M. Lanza and Samuel A. Wickline, "Targeted Ultrasonic Contrast Agents for Molecular Imaging and Therapy" Progress in Cardiovascular Diseases, vol. 44, No. 1,Jul./Aug. 2001, 13-31.
Krix, Martin et al., "Quantification of perfusion of liver tissue and metastases using a multivessel model for replenishment kinetics of ultrasound contrast agents," Ultrasound in Med. & Biol., vol. 30, No. 10, pp. 1355-1363, Aug. 11, 2004.

(Continued)

*Primary Examiner* — Unsu Jung
*Assistant Examiner* — Michael N Fisher
(74) *Attorney, Agent, or Firm* — Bryan A. Santarelli; Lane Powell, PC

(57) ABSTRACT

An embodiment analyzes a body part of a patient, which patient is perfused with a contrast agent that is capable of circulating within the patient and of being substantially immobilized on a biological target. An embodiment of a corresponding system provides an echo signal that is indicative of a response over time to an interrogation signal of the body part, fits the echo signal with a time model function that models an evolution over time of the contrast agent in the body part, the time model function including a combination of a circulation function that models the circulation of the contrast agent and a decay function that models a decay of the echo signal from the immobilized contrast agent, and estimates at least one kinetics indicator of the contrast agent from the time model function.

35 Claims, 11 Drawing Sheets

(56) References Cited

U.S. PATENT DOCUMENTS

| | | | |
|---|---|---|---|
| 5,583,902 A * | 12/1996 | Bae | 378/8 |
| 6,216,094 B1 * | 4/2001 | Fox Linton et al. | 702/100 |
| 6,445,945 B1 * | 9/2002 | Arsenault | 600/431 |
| 6,540,680 B1 * | 4/2003 | Kurosaki | 600/443 |
| 6,879,853 B2 * | 4/2005 | Meaney et al. | 600/420 |
| 7,069,068 B1 * | 6/2006 | Ostergaard | 600/420 |
| 2004/0172303 A1 * | 9/2004 | Declerck et al. | 705/2 |
| 2008/0139942 A1 * | 6/2008 | Gaud et al. | 600/458 |

FOREIGN PATENT DOCUMENTS

| | | |
|---|---|---|
| JP | 2000506398 | 5/2000 |
| JP | 2001178717 | 7/2001 |
| JP | 2007090075 | 4/2007 |
| JP | 2007536048 | 12/2007 |
| WO | 9115244 | 10/1991 |
| WO | 9409829 | 5/1994 |
| WO | 9516467 | 6/1995 |
| WO | 2004110279 | 12/2004 |
| WO | 2005116902 | 12/2005 |
| WO | 2006018433 | 2/2006 |
| WO | 2006067201 | 6/2006 |
| WO | 2006108868 A1 | 10/2006 |
| WO | 2007054544 | 5/2007 |
| WO | 2009083557 A1 | 7/2009 |
| WO | 2010058014 A1 | 5/2010 |
| WO | 2011110552 A1 | 9/2011 |

OTHER PUBLICATIONS

Linton, R.A.F. et al., "A new method of analyzing indicator dilution curves," Cardiovascular Research, vol. 30, pp. 930-938, 1995.
Rafter, Patrick et al., "Imaging technologies and techniques," Cardiology Clinics vol. 22, pp. 181-197, 2004.
International Search Report of May 16, 2011 for PCT/EP2011/053460 (WO11110552), international filing date of Mar. 8, 2011 for "Initialization of Fitting Parameters for Perfusion Assessment Based on Bolus Administration" 4 pages.
International Search Report of Apr. 20, 2009 for PCT/EP2008/068247 (WO09083557), international filing date of Dec. 23, 2008 for "Quantification Analysis of Immobilized Contrast Agent in Medicinal Imaging Application" 3 pages.
International Preliminary Report on Patentability of Sep. 11, 2012 for PCT/EP2011/053460 (WO11110552), international filing date of Mar. 8, 2011 for "Initialization of Fitting Parameters for Perfusion Assessment Based on Bolus Administration" 8 pages.
International Preliminary Report on Patentability of Jun. 29, 2010 for PCT/EP2008/068247 (WO09083557), international filing date of Dec. 23, 2008 for "Quantification Analysis of Immobilized Contrast Agent in Medicinal Imaging Application" 7 pages.
International Search Report for International Application Serial No. PCT/EP2008/068247, European Patent Office, Apr. 20, 2009.

* cited by examiner

QUANTIFICATION ANALYSIS OF IMMOBILIZED CONTRAST AGENT IN MEDICAL IMAGING APPLICATIONS

PRIORITY CLAIM

The present application is a national phase application filed pursuant to 35 USC §371 of International Patent Application Serial No. PCT/EP2008/068247, filed Dec. 23, 2008; which further claims the benefit of European Patent Application 07124133.5, filed Dec. 28, 2007; all of the foregoing applications are incorporated herein by reference in their entireties.

TECHNICAL FIELD

A solution according to an embodiment of the present invention relates to the medical imaging field. More specifically, an embodiment relates to medical imaging applications based on contrast agents adapted to be immobilized on biological targets.

BACKGROUND

Medical imaging is a well-established technique (in the field of equipments for medical applications), which allows analyzing a body part of a patient in a substantially non-invasive manner. A specific medical imaging technique is based on the administration of an ultrasound contrast agent (UCA) to the patient (for example, consisting of a suspension of phospholipid-stabilized gas-filled microbubbles); the contrast agent acts as an efficient ultrasound reflector, so that it can be easily detected by applying ultrasound waves and measuring a resulting echo signal. The echo signal so obtained may be used to estimate different physiologic characteristics of the body part; for example, as the contrast agent flows at the same velocity as the blood in the patient, its tracking provides a representation of a perfusion of the blood in the body part (from which it is possible to derive haemodynamic and/or morphological information about the body part).

Target-specific contrast agents, adapted to reach a specific (biological) target and then remain immobilized thereon, have also been proposed in the last years for characterizing and facilitating the detection of specific pathologies. Particularly, a target-specific contrast agent is capable of attaching to the corresponding target—such as particular tissues or receptors—by means of a specific interaction therewith; for example, the desired behavior may be achieved by incorporating a target-specific ligand (e.g., capable of interacting with inflammatory or tumoral tissues) in the formulation of the contrast agent. In addition, contrast agents may also be conveyed or accumulated to a specific location, such as tissues or organs, by means of a non-specific interaction therewith; for example, the contrast agent may be recognized as a foreign substance by the immune system of the patient and then transported to the liver for its metabolism and elimination. In any case, the detection and the quantification of the above-mentioned targeted contrast agent immobilized on the desired target (either with specific or non-specific interaction) provides valuable information about the presence, quantity, functionality, and spatial distribution of the target; for example, this information may allow distinguishing pathologies that would be otherwise difficult to identify.

However, the detection and quantification of the immobilized contrast agent may be hindered by the fact that only a relatively small fraction of the total amount of the targeted contrast agent actually reaches the target and remains immobilized thereon; most of the targeted contrast agent continues instead to circulate for quite a long time (e.g., several minutes)—for example, until it is filtered out by the lungs and/or in the liver of the patient. The echo signal that is measured is then the result of both a contribution of the immobilized targeted contrast agent and a contribution of the circulating or free-flowing targeted contrast agent. Therefore, it may be quite difficult to extract from this echo signal the desired information about the immobilized contrast agent (so as to detect and quantify it).

A solution known in the art that tackles this problem is disclosed in "Albumin Microbubble Persistence During Myocardial Contrast Echocardiography Is Associated With Microvascular Endothelial Glycocalyx Damage"—Jonathan R. Lindner, Suad Ismail, William D. Spotnitz, Danny M. Skyba, Ananda R. Jayaweera and Sanjiv Kaul—Circulation 1998; 98; 2187-2194 by American Heart Association. 7272 Greenville Avenue, Dallas, Tex. 72514—Print ISSN: 0009-7322. Online ISSN: 1524-4539, which is incorporated by reference. Particularly, this document proposes fitting the echo signal by a mathematical model that consists of the weighted sum of a $\gamma$-variate function (modeling the circulation of the contrast agent) and the integral of the same $\gamma$-variate (representing the fraction of the targeted contrast agent that immobilizes).

However, the solution described in the above listed document may be unsatisfactory. Indeed, experimental results have shown that the obtained results do not correctly represent the actual rate of the immobilization of the contrast agent. Therefore, it may not be possible to detect and quantify the immobilized contrast agent with an acceptable degree of accuracy. This prevents the clinical application of the known analysis techniques based on the use of targeted contrast agents.

SUMMARY

In its general terms a solution according to an embodiment of the present invention is based on the idea of taking into account a decay of the echo signal from the immobilized contrast agent in the modeling.

Particularly, an embodiment of the invention proposes a system (for example, an ultrasound scanner or a computer associated therewith) for analyzing a body part of a patient that is perfused with a contrast agent; the contrast agent (e.g., of the target-specific type) is capable of circulating within the patient and of being substantially immobilized on a biological target. The system comprises means for providing an echo signal, which is indicative of a response over time to an interrogation signal of the body part (e.g., an echo-power for ultrasound waves). The system then comprises means for associating the echo signal with a model function of time, which models an evolution over time of the contrast agent in the body part (e.g., by determining the instance of the model function that best fits the echo signal); the model function includes a combination of a circulation function modeling the circulation of the contrast agent (e.g., based on a log normal distribution function), and a decay function modeling a decay of the echo signal from the immobilized contrast agent. Means is then provided for estimating one or more kinetics indicators of the contrast agent from the model function (e.g., an immobilization rate that quantifies the immobilization of the contrast agent).

In an embodiment of the invention, the contrast agent is administered as a bolus.

In a proposed embodiment, the model function further includes an immobilization function modeling the immobilization of the contrast agent (i.e., it is based on a combination of the circulation function, the decay function, and the immobilization function).

The model function may include the sum of the circulation function with the product of an immobilization parameter (representing a constant immobilization rate of the contrast agent) by the convolution product between the circulation function and the decay function.

For example, it may be possible to calculate an immobilization indicator (representing the immobilization of the contrast agent as a percentage of the circulating contrast agent) by multiplying a mean transit time of the circulating contrast agent (estimated from the circulation function) by the immobilization parameter.

Alternatively, the model function may be simplified by considering it as corresponding to the circulation function alone until the reaching of a time offset; for each instant after the time offset, the model function instead includes a product between a value of the circulation function at the time offset by the decay function referred to the time offset (taken as a time origin).

The time offset may be set according to a time to peak that is required by the echo signal to reach its absolute peak (e.g., a predefined percentage thereof).

In an embodiment of the invention, the decay function is an exponential function characterized by a decay parameter, which represents a time constant of the decay of the echo signal from the immobilized contrast agent.

Alternatively, it may also be possible to use a decay function based on two or more time constants.

For example, the circulation function may be based on a log normal distribution function.

As a further embodiment, the fitting of the echo signal by the model function is performed in two optimization steps. Particularly, a first optimization step is based on an analysis of a circulating contrast agent (for example, a previous administration of a non-targeted contrast agent or a subsequent administration of the same targeted contrast agent after an inhibition of the interaction with its target); the result of the first optimization step is used to facilitate a second optimization step based on the administration of the targeted contrast agent.

Alternatively, a first and a second similar optimization steps may be performed on the same echo signal for the targeted contrast agent (over an initial portion thereof and over its whole extension, respectively).

The initial portion of the echo signal may be selected according to the time to peak (e.g., a time equal to a predefined multiple thereof).

A way to further improve the obtained result may be assigning different weights to the values of the echo signal in the initial portion and in the remaining portion thereof during the second optimization step.

In an embodiment of the invention, the parameters (of the circulation function) that are determined in the first optimization steps are used to constrain the corresponding parameters of the model function in the second optimization step within a predefined range around them.

Another embodiment of the invention proposes a method for analyzing a body part of a patient, which is perfused with a contrast agent; the contrast agent is capable of circulating within the patient and of being substantially immobilized on a biological target. The method comprises a first step of providing an echo signal, which is indicative of a response over time to an interrogation signal of the body part. The method then comprises the step of associating the echo signal with a model function of time, which models an evolution over time of the contrast agent in the body part; the model function includes a combination of a circulation function modeling the circulation of the contrast agent, and a decay function modeling a decay of the echo signal from the immobilized contrast agent. It is then possible to estimate one or more kinetics indicators of the contrast agent from the model function.

The same or similar features (pointed out with reference to the system) may apply mutatis mutandi to the method.

Another embodiment of the present invention proposes a software program for performing the method.

A further embodiment of the present invention proposes a computer program product including a computer-usable medium embodying this computer program.

BRIEF DESCRIPTION OF THE DRAWINGS

The solution according to one or more embodiments of invention, as well as further features and the advantages of these and other embodiments, will be best understood with reference to the following detailed description, given purely by way of a non-restrictive indication, to be read in conjunction with the accompanying drawings, in which.

DETAILED DESCRIPTION

Figure 1:
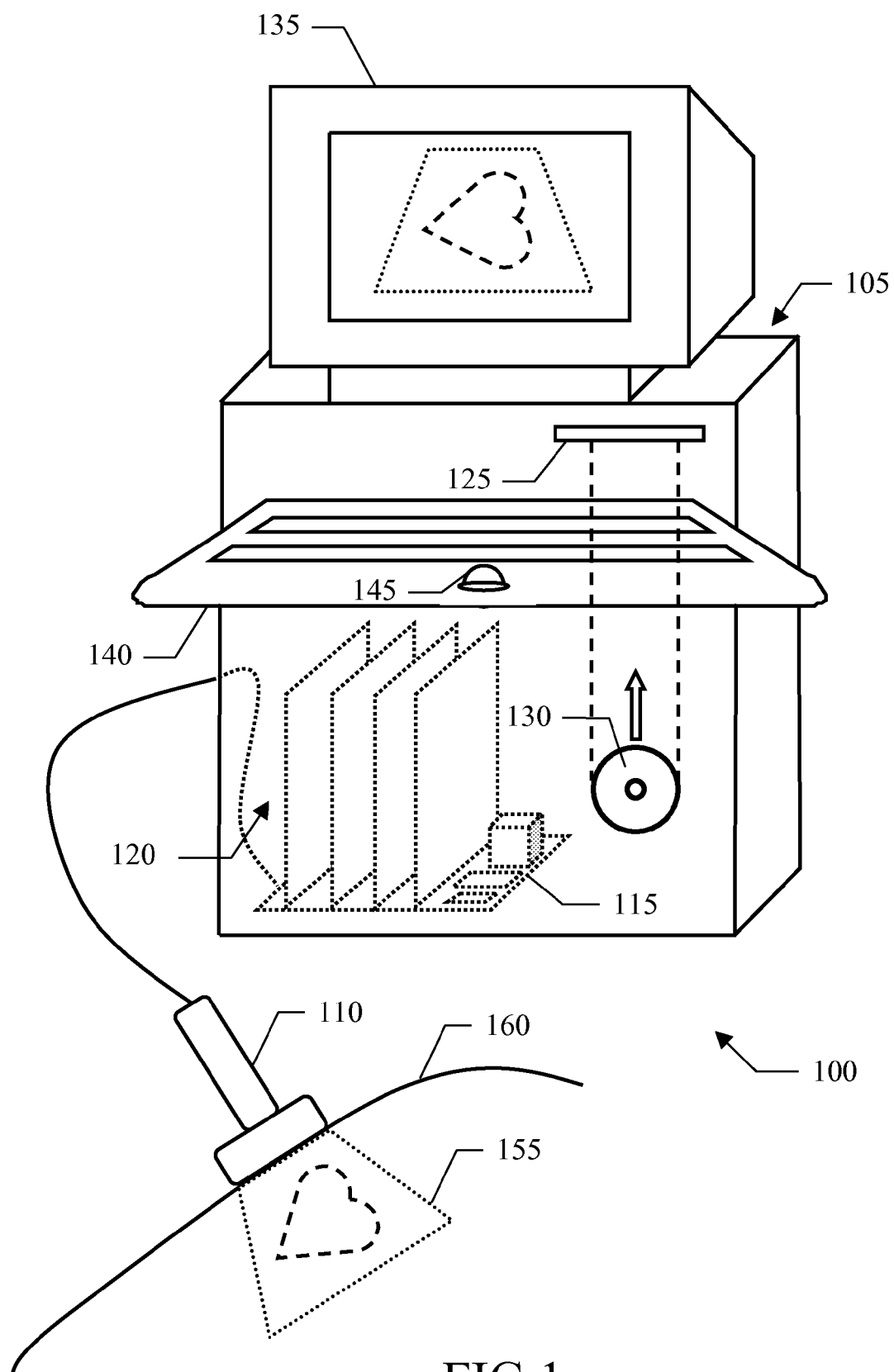
FIG. 1 is a pictorial representation of an ultrasound scanner in which a solution according to an embodiment of the invention is applicable.

With reference in particular to FIG. 1, an embodiment of a medical imaging system consisting of an ultrasound scanner 100 is illustrated. The ultrasound scanner 100 includes a central unit 105 and a hand-held transmit-receive imaging probe 110 (for example, of the array type). The imaging probe 110 transmits ultrasound waves consisting of a sequence of pulses (for example, having a center frequency between 1 and 50 MHz), and receives a raw radio-frequency (RF) echo signal resulting from the reflection of the ultrasound pulses; for this purpose, the imaging probe 110 is provided with a transmit/receive multiplexer, which allows using the imaging probe 110 in the above-mentioned pulse-echo mode.

The central unit 105 houses a motherboard 115, on which the electronic circuits controlling operation of the ultrasound scanner 100 (for example, a microprocessor, a working memory and a hard-disk drive) are mounted. Moreover, one or more daughter boards (denoted as a whole with 120) are plugged on the motherboard 115; the daughter boards 120 provide the electronic circuits for driving the imaging probe 110 and for processing the received echo signal. The ultrasound scanner 100 can also be equipped with a drive 125 for reading removable disks 130 (such as CD-ROMs). A monitor 135 displays images relating to an analysis process that is in progress. Operation of the ultrasound scanner 100 is controlled by means of a keyboard 140, which is connected to the central unit 105 in a conventional manner; preferably, the keyboard 140 is provided with a trackball 145 that is used to manipulate the position of a pointer (not shown in the figure) on a screen of the monitor 135.

The ultrasound scanner 100 is used to analyze a body part 155 of a patient 160. For this purpose, a contrast agent (acting as an efficient ultrasound reflector) is administered to the patient 160. For example, the contrast agent consists of a suspension of gas bubbles in a liquid carrier; typically, the gas bubbles have diameters on the order of 0.1-5 µm, so as to allow them to pass through the capillaries of the patient. The gas bubbles are generally stabilized by entraining or encapsulating the gas or a precursor thereof into a variety of systems, including emulsifiers, oils, thickeners, sugars, proteins or polymers; stabilized gas bubbles are generally referred to as gas-filled microvesicles. The microvesicles include gas bubbles dispersed in an aqueous medium and bound at the gas/liquid interface by a very thin envelope involving a surfactant, i.e., an amphiphilic material (also known as microbubbles). Alternatively, the microvesicles include gas bubbles that are surrounded by a solid material envelope formed of lipids or of natural or synthetic polymers (also known as microballoons or microcapsules). Another kind of contrast agent includes a suspension of porous microparticles of polymers or other solids, which carry gas bubbles entrapped within the pores of the microparticles. Examples of suitable aqueous suspensions of microvesicles, in particular microbubbles and microballoons, and of the preparation thereof are described in EP-A-0458745, WO-A-91/15244, EP-A-0554213, WO-A-94/09829 and WO-A-95/16467 (the entire disclosures of which are herein incorporated by reference). An example of a commercial contrast agent comprising gas-filled microvesicles is SonoVue® by Bracco International BV.

The contrast agent may be a target-specific contrast agent in an embodiment. The target-specific contrast agent is substantially free to circulate within the patient; however, the target-specific contrast agent is also capable of being immobilized on a selected (biological) target, so as to remain in a substantially fixed position for a certain period. For this purpose, the target-specific contrast agent is formulated in such a way as to bind selectively to the desired target by means of a specific interaction therewith. For example, this behavior may be achieved by incorporating a target-specific ligand capable of selectively binding (for example, through biochemical affinity and/or electrostatic interaction) to a desired tissue or receptor. Examples of target-specific ligands (which may be inserted into a membrane of the microbubbles) are monoclonal antibodies, peptides, or polysaccharides. The term tissue includes (within its meaning) individual cells as well as aggregates of cells, such as membranes or organs. The term refers to either normal (healthy) or abnormal (pathological) cells or aggregates of cells. Examples of tissue are myocardial tissue (including myocardial cells and cardiomyocytes), membranous tissue (such as endothelium and epithelium), and connective tissue; examples of pathological tissue are infracted heart tissue, blood clots, atherosclerotic plaques, inflammatory tissue and tumoral tissue. The receptors include any molecular structure located on the tissue (for example, within the cells or on their surfaces), which is capable to selectively bind to a specific substance. Exemplary receptors are glycoprotein GPIIbIIIa or fibrin (for example, located in blood clots or thrombi), P-Selectin (for example, located on activated endothelium of inflamed tissue) or KDR (for example, located in tumoral tissue). Examples of suitable target-specific contrast agents and of target-specific ligands are described in "G. M. Lanza and S. A. Wickline, Targeted Ultrasonic Contrast Agents for Molecular Imaging and Therapy, Progress in Cardiovascular Diseases, 44(1), 2001, 13-31", and in WO-A-2006018433 (the entire disclosures of which are herein incorporated by reference).

The contrast agent may be administered to the patient 160 intravenously by injection. For example, the contrast agent may be administered as a bolus (i.e., a single dose provided over a short period of time, typically of the order of 2-20 seconds); the contrast agent may then move within the vascular system of the patient 160, so as to perfuse the body part 155. The bolus administration is very simple, and it may be carried out by hand (for example, using a syringe); moreover, it may require a small amount of contrast agent.

During an embodiment of the analysis process, the imaging probe 110 is placed in contact with the skin of the patient 160 in the area of the body part 155. A series of ultrasound pulses with low acoustic energy is applied to the body part 155 (for example, with a mechanical index MI=0.01-0.1, so as to involve a negligible destruction of the contrast agent). The echo signal that is received in response to the ultrasound pulses over time is recorded continuously (for example, at time intervals of 30-80 ms); in this way, the recorded echo signal tracks an evolution of the contrast agent in the body part 155 over time.

The echo signal so obtained may be associated with an instance of a model function of time, which is defined by corresponding values of a set of parameters thereof. The type of model function is selected so as to exhibit a pattern that is adapted to model the nature of evolution of the echo signal under analysis; the actual instance of the model function to be associated to the specific recorded echo signal is then determined by an optimization process, which selects the values of its parameters that provide the best fitting of the recorded echo signal (hereinafter, both the type of model function and its instance and both the corresponding parameters and their values will be indicated generically as model function and parameters, respectively, for the sake of simplicity). The parameters of the model function may then be used to estimate a number of kinetics indicators, which provide information about (haemodynamic and/or morphological) characteristics of the body part 155; in this case (wherein a targeted contrast agent is administered) these kinetics indicators also provide useful information about the presence and the quantity of the target in the body part 155.

Figure 2:
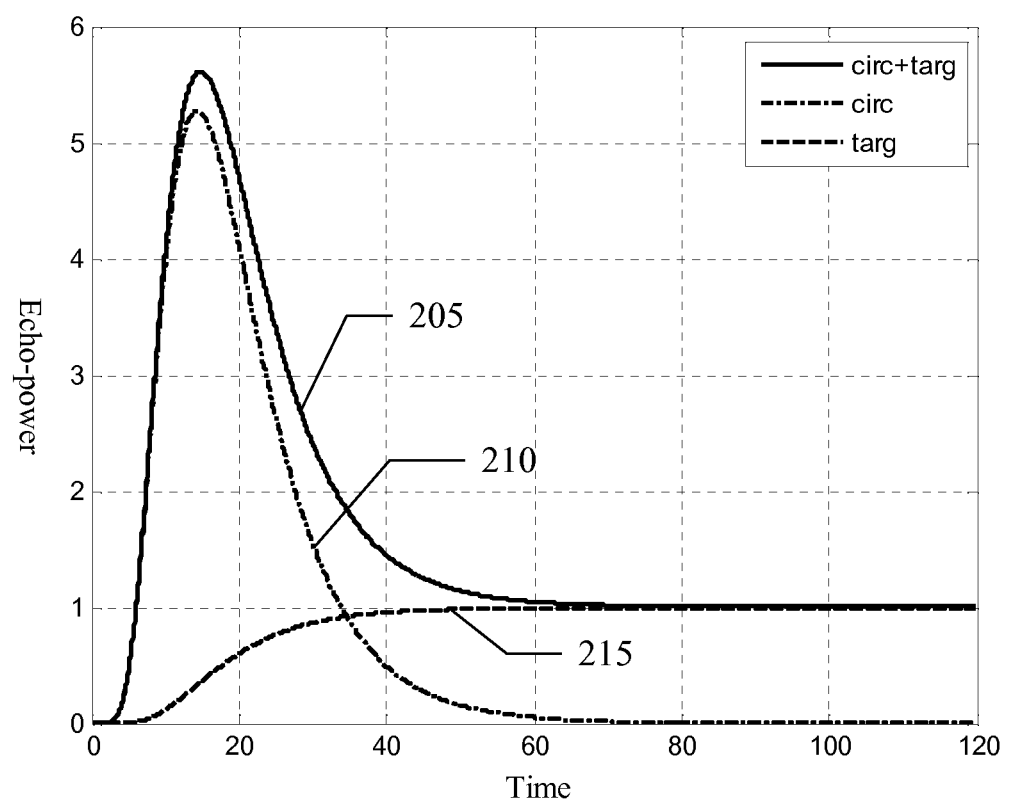
FIG. 2 shows an exemplary model function that has been proposed in the prior art to model the evolution over time of an echo signal recorded with the ultrasound scanner.

With reference now to FIG. 2, an exemplary model function that has been proposed in the prior art to model the evolution of the echo signal (for example, in the above-mentioned document by Lindner et al.) is illustrated in a diagram, which plots the values of the power of the echo signal, or echo-power signal (in terms of arbitrary units, or a.u.) against time (in seconds). The model function proposed in this document—represented in the figure with a model curve 205—results from the combination of two different contributions (hereinafter, each function and the corresponding curve will be denoted with the same reference).

Particularly, a contribution is given by a circulation function that is represented by a circulation curve 210; the circulation function 210 models the (free) circulation of the contrast agent. For example, when the contrast agent is administered as a bolus (as in the case at issue), the circulation curve 210 has an initial portion wherein the echo signal increases towards a rounded peak, as a result of a wash-in phase of the contrast agent following its administration; once the echo signal has reached its maximum value, it starts decreasing towards zero as a result of a wash-out phase of the contrast agent.

Another contribution to the model function 205 is given by an immobilization function that is represented by an immobilization curve 215; the immobilization function 215 instead models the immobilization of the contrast agent (on the corresponding target). As can be seen, the immobilization curve 215 exhibits a fast increase rate during the wash-in phase (when a high amount of contrast agent reaches the body part with a fraction thereof that remains immobilized), and it continues to increase at a lower rate during the wash-out phase (when a lower amount of contrast agent reaches the body part); the immobilization curve 215 reaches its maximum value at the end of the perfusion process (when no further contrast agent reaches the body part), and it then maintains this value later on.

Therefore, the model function 205 (resulting from the sum of the circulation function 210 with the immobilization function 215) is slightly higher than the circulation function 210 during the wash-in phase (because of the additional contribution of the immobilized contrast agent that remains in the body part). The model function 205 then tends towards the immobilization function 215 during the wash-out phase (since its contribution becomes predominant as the circulation of the contrast agent reduces), until becoming coincident with it at the end of the perfusion process.

However (as it will be apparent in the following), the model function 205 may not be effective in modeling the actual evolution of the echo signal accurately. Indeed, in practice it may not be possible to observe a strictly stationary echo signal after the completion of the perfusion process.

Conversely, far better results may be achieved by taking into account a decay of the echo signal from the immobilized contrast agent as well. For example, the decay may be caused by the immobilized contrast agent that detaches after a certain period of time. Typically, this may be due to a non-specific interaction of the contrast agent with a passive target consisting of any other biological elements (i.e., tissues or receptors) different from the actual (active) target thereof. For example, the contrast agent may attach to a receptor that is similar to the active target (i.e., including a component interacting with the contrast agent). As another example, the contrast agent may be modified by the patient's immune system (for example, when it is recognized as a non-self component of the blood, thus being opsonized by blood proteins and then phagocytosed by monocytes or macrophage); in this case, the modified contrast agent may loose its specificity or it may acquire a weaker specificity with other biological elements different from the active target. Moreover, the contrast agent may also be temporarily immobilized at locations having a reduced specific interaction with it. For example, this may be due to a low concentration of the receptors for the contrast agent. Another cause of the decay of the echo signal from the immobilized contrast agent is its disappearance due to limitations in natural stability of the contrast agent. Moreover, the applied ultrasound pulses may destroy the immobilized contrast agent. A further disturbing factor occurs when the contrast agent moves very slowly, so as to appear apparently immobilized (for example, at the micro-vascular level). In any case, the echo signal from the immobilized contrast agent may also decay because the agent looses its echogenicity (at least in part), so that the response to the ultrasound pulses decreases over time even though the amount of immobilized contrast agent remains constant.

Therefore, in the solution according to an embodiment of the present invention (as described in a detail in the following), the model function includes an additional contribution for the decay of the echo signal from the immobilized contrast agent (besides the one for the circulation of the contrast agent and possibly the one for its immobilization).

Figure 3:
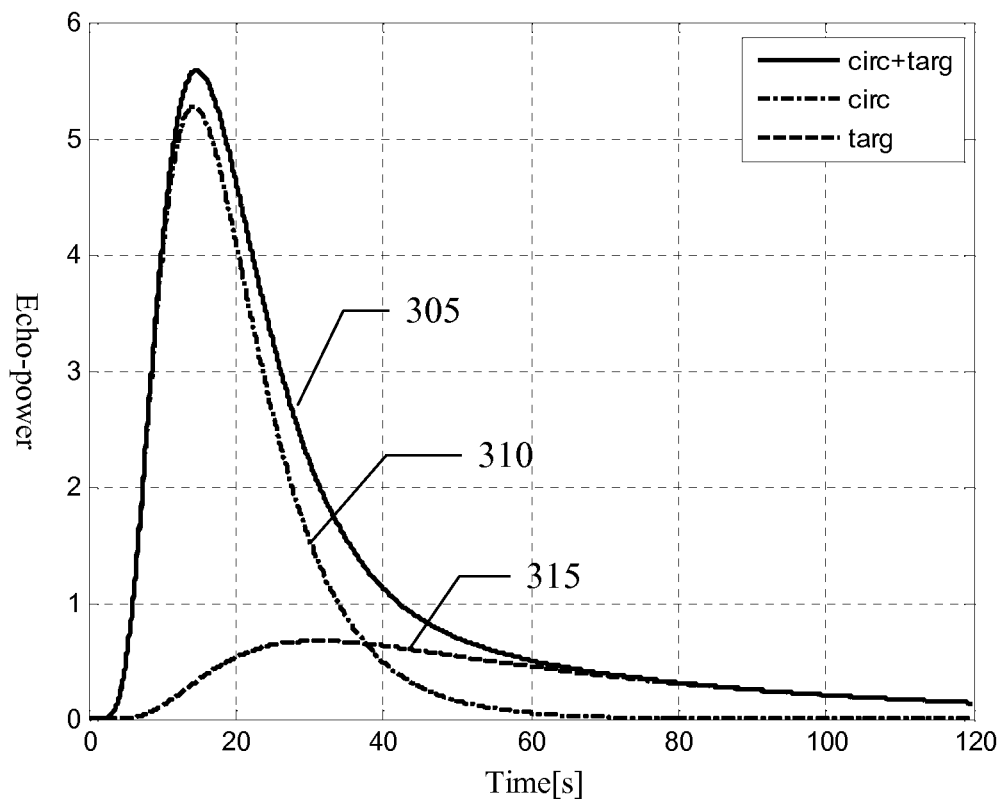
FIG. 3 shows an exemplary model function according to an embodiment of the invention.

For instance, an exemplary model function according to an embodiment of invention is illustrated in FIG. 3. The proposed model function—represented in the figure with a model curve 305—results from the combination of three different contributions.

Particularly, a contribution is given by a circulation function that is represented with a circulation curve 310 (the same as the circulation curve described above).

Another contribution to the model function 305 is given by a dynamic immobilization function that is represented with a dynamic immobilization curve 315. The dynamic immobilization function 315 now models both the immobilization of the contrast agent and the decay of its echo signal. For this purpose, the dynamic immobilization function 315 in turn includes the contribution of a permanent immobilization function and a decay function. The permanent immobilization function models the immobilization of the contrast agent (the same as the immobilization function described above). The decay function instead models the decay of the echo signal from the immobilized contrast agent (due to its detachment, disappearance, destruction, slow movement, and/or lower echogenicity). As a result, after a short period in which the dynamic immobilization curve 315 coincides with the immobilization curve described above, the dynamic immobilization curve 315 now exhibits a slower increase during the wash-in phase and the beginning of the wash-out phase (as soon as the echo signal from a fraction of the contrast agent previously immobilized starts decaying). As the perfusion process approaches its completion (with a lower amount of contrast agent that reaches the body part and then remains immobilized) the dynamic immobilization curve 315 decreases tending to zero (when the decay of the echo signal from the immobilized contrast agent exceeds its increase due to the contrast agent that immobilizes).

Therefore, the model function 305 (resulting from the sum of the circulation function 310 with the dynamic immobilization function 315) is again slightly higher than the circulation function 310 during the wash-in phase (because of the additional contribution of the immobilized contrast agent that remains in the body part minus the one of its echo signal that decays). The model function 305 then tends towards the dynamic immobilization function 315 during the wash-out phase (since its contribution becomes predominant as the circulation of the contrast agent reduces), until becoming coincident with it at the end of the perfusion process. As a result, the model function 305 is no longer stationary after the completion of the perfusion process, so as to take into account both the contribution of the contrast agent that immobilizes and the decay of its echo signal.

An embodiment of the proposed solution has been found to model the real evolution of the echo signal with high precision. Particularly, the parameters that are obtained when the echo signal is fitted by this model function 305 correctly represent the rate of the immobilization of the contrast agent. Therefore, it is now possible to detect and quantify the immobilized contrast agent with a high degree of accuracy. All of the above fosters the clinical application of the analysis techniques based on the use of targeted contrast agents. This is especially useful for the assessment of diseases like cancer, where neoangiogenesis accompanying tumor growth is associated with the presence of specific markers—for example, vascular endothelial growth factor (VEGF) receptors. By designing a contrast agent comprising ligands targeted to such receptors—for example, kinase insert domain receptor (KDR or VEGFR-2)—an embodiment of the proposed solution may be applied for the assessment of neoangiogenesis. Another possible application is in the assessment of neoangiogenesis due to inflammatory processes associated with various pathologies (such as infection, injury, and the like).

More specifically, in an embodiment of the invention the model function is given by the sum of the circulation function and the dynamic immobilization function, i.e.:

$$P(t) = c(t) + b(t), \quad (1)$$

where $P(t)$, $c(t)$ and $b(t)$ are the model function, the circulation function and the dynamic immobilization function, respectively, with the time (t) measured from the beginning of the perfusion process.

In order to express the dynamic immobilization function $b(t)$, it is assumed that the amount of contrast agent that immobilizes at any instant, per unit time, is proportional to its instantaneous concentration—according to a constant immobilization rate. Under this hypothesis, the immobilized contrast agent at any instant is given by the product of the immobilization rate by the cumulative amount of the contrast agent that reached the body part from the beginning of the perfusion process as reduced by the decay of the echo signal from the immobilized contrast agent that occurred in the meanwhile. Assuming that the rate of decay of the echo signal from the immobilized contrast agent is independent of its concentration, the instantaneous concentration of the immobilized contrast agent at any instant is proportional to the convolution product between the circulation function and the decay function. Therefore, the dynamic immobilization function $b(t)$ may be expressed as:

$$b(t) = \alpha \cdot c(t) * d(t) = \alpha \int_{-\infty}^{\infty} c(t') d(t - t') dt', \quad (2)$$

where $\alpha$ is an immobilization parameter that represents the immobilization rate of the contrast agent, $d(t)$ is the decay function, and $*$ is the convolution operator. In this case, where $c(t)=0$ for $t<0$ and $d(t)=0$ for $t<0$—i.e., $d(t-t')=0$ for $t'>t$, the dynamic immobilization function $b(t)$ becomes:

$$b(t) = \alpha \int_{-\infty}^{\infty} c(t') d(t - t') dt' = \alpha \int_{0}^{t} c(t') d(t - t') dt', \quad (3)$$

and then the whole model function $P(t)$ of equation (1) is:

$$P(t) = c(t) + b(t) = c(t) + \alpha \int_{0}^{t} c(t') d(t - t') dt', \quad (4)$$

The decay function $d(t)$ may be defined by assuming that the echo signal from the immobilized contrast agent decays with an exponential law (for $t \geq 0$) according to a single time constant, i.e.:

$$d(t) = e^{-t/\Delta}, \quad (5)$$

where $\Delta$ is a decay parameter the represents the time constant of the decay of the echo signal from the immobilized contrast agent. With these hypotheses, the whole model function $P(t)$ of equation (4) becomes:

$$P(t) = c(t) + \alpha \int_{0}^{t} c(t') d(t - t') dt' \quad (6)$$
$$= c(t) + \alpha \int_{0}^{t} c(t') e^{-(t-t')/\Delta} dt',$$

For example, when the contrast agent is administered as a bolus, like in the case at issue, a realistic circulation function $c(t)$ is based on a log normal function (i.e., a normal distribution function of the natural logarithm of an independent variable), i.e.:

$$c(t) = A \cdot \log n(t) = A \cdot \frac{e^{-\frac{[ln(t)-m]^2}{2s^2}}}{t \cdot s \sqrt{2\pi}}, \quad (7)$$

where A is an amplitude parameter (which may be interpreted as proportional to the blood volume in the body part), and the parameters m and s are the mean and standard deviation of the distribution of the variable $ln(t)$, respectively. In this case, the model function $P(t)$ of equation (2) is:

$$P(t) = A \cdot [\log n(t) + \alpha \log n(t) * d(t)] \quad (8)$$
$$= A \cdot \left[\log n(t) + \alpha \int_{0}^{t} \log n(t) e^{-(t-t')/\Delta} dt\right].$$

The proposed model function $P(t)$—modeling the general condition in which the contrast agent immobilizes and then its echo signal decays (i.e., $\alpha>0$ and $0<\Delta<\infty$)—also correctly models the limit conditions when the contrast agent does not immobilize (i.e., $\alpha=0$) or when the echo signal of the immobilized contrast agent does not decay (i.e., $\alpha>0$ and $\Delta\to\infty$). Indeed, when the contrast agent is substantially free to circulate—for example, because the body part does not include the corresponding target or a non-targeted contrast agent is used—the model function $P(t)$ of equation (2) reduces to the circulation function $c(t)$, since:

$$P(t) = c(t) + 0 \cdot c(t) * d(t) = c(t). \quad (9)$$

Conversely, when the decay of the echo signal from the immobilized contrast agent may be deemed negligible the decay function $d(t)$ becomes the Heaviside step function defined as:

$$H(t) = \begin{cases} 0 & t < 0 \\ 1 & t \geq 0; \end{cases} \quad (10)$$

therefore, the model function $P(t)$ of equation (2) becomes:

$$P(t) = c(t) + \alpha c(t) * H(t) \quad (11)$$
$$\equiv c(t) + \alpha \int_{-\infty}^{\infty} c(t') H(t - t') dt'$$
$$= c(t) + \alpha \int_{0}^{t} c(t') dt',$$

because c(t')=0 for t'<0 and H(t−t')=0 for t'>t. Particularly, when the circulation function c(t)=A·log n(t)—see equation (7)—the same expressions may be rewritten as:

$$P(t) = A \cdot \log n(t) + \alpha \int_0^t A \cdot \log n(t')dt' \qquad (12)$$
$$= A \cdot [\log n(t) + \alpha \cdot \log perf(t)],$$

where log perf(t) is a cumulative log normal distribution function given by:

$$\log perf(t) = \frac{1}{2} \cdot \left(1 + \mathrm{erf}\left(\frac{\ln(t) - m}{s\sqrt{2}}\right)\right), \qquad (13)$$

with erf( ) equal to the error function, defined in terms of an arbitrary variable q as:

$$\mathrm{erf}(q) = \frac{2}{\sqrt{\pi}} \int_0^q e^{-u^2} du. \qquad (14)$$

The parameters of the model function P(t) (which fit the recorded echo signal) may be used to calculate kinetics indicators representing haemodynamic and/or morphological characteristics of the body part as usual. Examples of kinetics indicators of the haemodynamic characteristics are relative blood volume in the body part in proportion to the amplitude parameter A, and a mean transit time of the contrast agent determined from the parameters m and s as $$\tau = e^{m + \frac{s^2}{2}};$$

in this way, it may also be possible to calculate a mean relative blood perfusion index as $\phi = A/\tau$. Examples of kinetics indicators of the morphological characteristics are, for example, a variance $\sigma^2$ of the transit time distribution—defined by $\sigma^2 = e^{s^2+2m} \cdot (e^{s^2}-1)$—or a skewness $\gamma$ thereof—defined by $\gamma = \sqrt{e^{s^2}-1} \cdot (2+e^{s^2})$. Moreover, in this case the immobilization parameter $\sigma$ may also provide a good estimate of the immobilization rate of the contrast agent, and the decay parameter $\Delta$ provides a good estimate of the time constant of the decay of the echo signal from the immobilized contrast agent. The values so obtained may also be combined among them in any way. For example, a particularly interesting combination is the product of the immobilization parameter $\alpha$ by the mean transit time $\tau$, which represents the fraction of contrast agent having perfused the body part ultimately assessed as being immobilized on its target (rather than the immobilization parameter $\alpha$ itself, which represents the same quantity but expressed per unit time).

The definition of the model function P(t) proposed in equation (4) may be simplified by considering negligible the contribution of the contrast agent that immobilizes in an initial phase of the perfusion process, so that in this phase the model function P(t) may be set to the circulation function c(t) alone. Later on, the rate of decay of the echo signal may also be considered as representative of the contrast agent that immobilized in the body part, so that in this phase the model function P(t) may be based only on the product of an initial value of the circulation function by the decay function. Therefore, an alternative model function P(t) may be considered:

$$P(t) = \begin{cases} c(t) & t < t_0 \\ c(t_0) \cdot d(t - t_0) & t \geq t_0, \end{cases} \qquad (15)$$

where $t_0$ is a time offset that is used to define when the decay of the echo signal begins to be taken into account. The time offset $t_0$ may be set according to a time to peak $t_p$ that is required by the echo signal to reach its peak (i.e., the maximum value). For example, the time offset $t_0$ may be set to the instant when the echo signal falls below a predefined percentage of its maximum value (for example, 90-80%) during the wash-out phase. This embodiment further facilitates the fitting of the echo signal by the model function P(t), still maintaining a high degree of accuracy.

In another embodiment of the invention, an alternative decay function d(t) may be defined, for t≥0, with a bi-exponential function having two time constants, i.e.:

$$d(t) = B \cdot e^{-t/\Delta_1} + (1-B) \cdot e^{-t/\Delta_2}, \qquad (16)$$

where $\Delta_1$ and $\Delta_2$ are two decay parameters (which represent different time constants of corresponding categories of decay of the echo signal from the immobilized contrast agent), and B (with 0≤B≤1) is a weight parameter (which represents the relative weights of the two categories of decay of the echo signal from the immobilized contrast agent). In this case, the time constant of the decay of the contrast agent may be estimated according to a combination of the decay parameters $\Delta_1$ and $\Delta_2$—for example, by setting it to $B \cdot \Delta_1 + (1-B) \cdot \Delta_2$. This alternative definition of the decay function d(t) may further improve the accuracy of the obtained results.

As a further improvement, the fitting of the echo signal by the model function P(t) may be performed in two optimization steps. Particularly, in a first optimization step another administration of contrast agent is applied to the patient. This contrast agent (referred to as control contrast agent) should be substantially free to circulate within the patient without immobilizing on any target; the control contrast agent is selected so as to provide a circulation behavior very similar to the one of the (targeted) contrast agent at issue. This result may be achieved by a previous administration of a non-targeted contrast agent with compatible characteristics. The same result may also be achieved by a subsequent administration of the same targeted contrast agent after an inhibition of its interaction with the corresponding target; for example, for this purpose it may be possible to saturate the target with free antibodies. The echo signal that is recorded in response to the administration of the control contrast agent is then fitted by an instance of the same circulation function c(t) described above (modeling its circulation); this provides the values of the corresponding parameters (A, m and s in the case of the log normal distribution function of equation (7)).

A second optimization step based on the administration of the actual targeted contrast agent may then be performed. However, the result of the first optimization step is now exploited to facilitate the fitting of the echo signal that is recorded in response to the administration of the targeted control contrast agent by the model function P(t). Indeed, the instance of the circulation function c(t) included in the model function P(t) is similar to the one being used to fit the echo signal of the control contrast agent (since their kinetics are similar); therefore, the values of the corresponding parameters A, m and s determined above provide a first estimate of their values in the model function P(t). For example, the parameters A, m and s for the second optimization step may be initialized to the corresponding values determined in the first optimization step, and then constrained to vary during the second optimization step within a predefined range. This constraint range of each parameter may be expressed as a percentage of allowed variation around its initial value. The constrain range may be set to ±50%, for example to ±30% for the amplitude parameter A; the constraint range may instead be set to ±30%, for example to ±15% for the parameters m and s. In this way, the second optimization step may be focused on the determination of the immobilization parameter α and the decay parameter Δ alone. This avoids any ambiguities in the results of the optimization process, which might be caused by the use of an excessive number of parameters to be determined at the same time (i.e., five in the example at issue). Therefore, an embodiment of the proposed solution offers a higher accuracy in the determination of the parameters of the model function P(t), and then a more robust estimate of the corresponding kinetics indicators.

Alternatively, two successive optimization steps may be performed on the same echo signal that is recorded in response to the administration of the (targeted) contrast agent. Indeed, when only a small fraction of the contrast agent immobilizes in the body part, its contribution to the echo signal in the initial phase of the perfusion process is negligible (with respect to the contribution of the circulating contrast agent); therefore, the corresponding initial portion of the echo signal may be deemed representative of the circulation of the contrast agent alone with an acceptable degree of accuracy. As a result, in a first optimization step the initial portion of the echo signal is fitted by an instance of the circulation function c(t), so as to provide the values of the corresponding parameters A, m and s (in the case of the log normal distribution function). The initial portion of the echo signal may be selected according to the corresponding time to peak (required by the echo signal to reach its maximum value). For example, the initial portion of the echo signal may be defined from the beginning of the perfusion process up to a predefined multiple of the time to peak (for example, 1.5-2 times). A second optimization step is then performed to fit the whole echo signal by the model function P(t); for this purpose, the result of the first optimization step is exploited in the same manner as described above (for example, to initialize the parameters A, m and s for the second optimization step to the corresponding values determined in the first optimization step, and then constraining them to vary during the second optimization step within a predefined range). The above-described alternative may offer a slightly better accuracy in the determination of the parameters of the model function P(t) than a single optimization step with the complete P(t) model function does, and still may require only a single administration of the contrast agent.

An embodiment to further improve the obtained result is by assigning different weights to the values of the echo signal in its initial portion and to those in the remaining portion thereof during the second optimization step; particularly, a lower weight is assigned to the values in the initial portion and a higher weight (for example, equal to 2-4 times the lower weight) is assigned to the values in the remaining portion of the echo signal. For example, when the optimization process is based on the gradient descent algorithm, at each iteration of the optimization process there is determined a direction along which a difference between the model function P(t) and the echo signal decreases most rapidly (i.e., the corresponding gradient is lowest); the parameters are then updated in this direction for a next iteration of the optimization process (until the difference falls below an acceptable threshold). In this case, the difference is based on a weighted sum of the instantaneous squared differences between each value of the model function P(t) and the corresponding value of the echo signal (according to the weight of its portion of the echo signal). An embodiment of the proposed solution increases the relative contribution of the portion of the echo signal in which the immobilized contrast agent becomes predominant, compared to the circulating one.

Figure 4A:
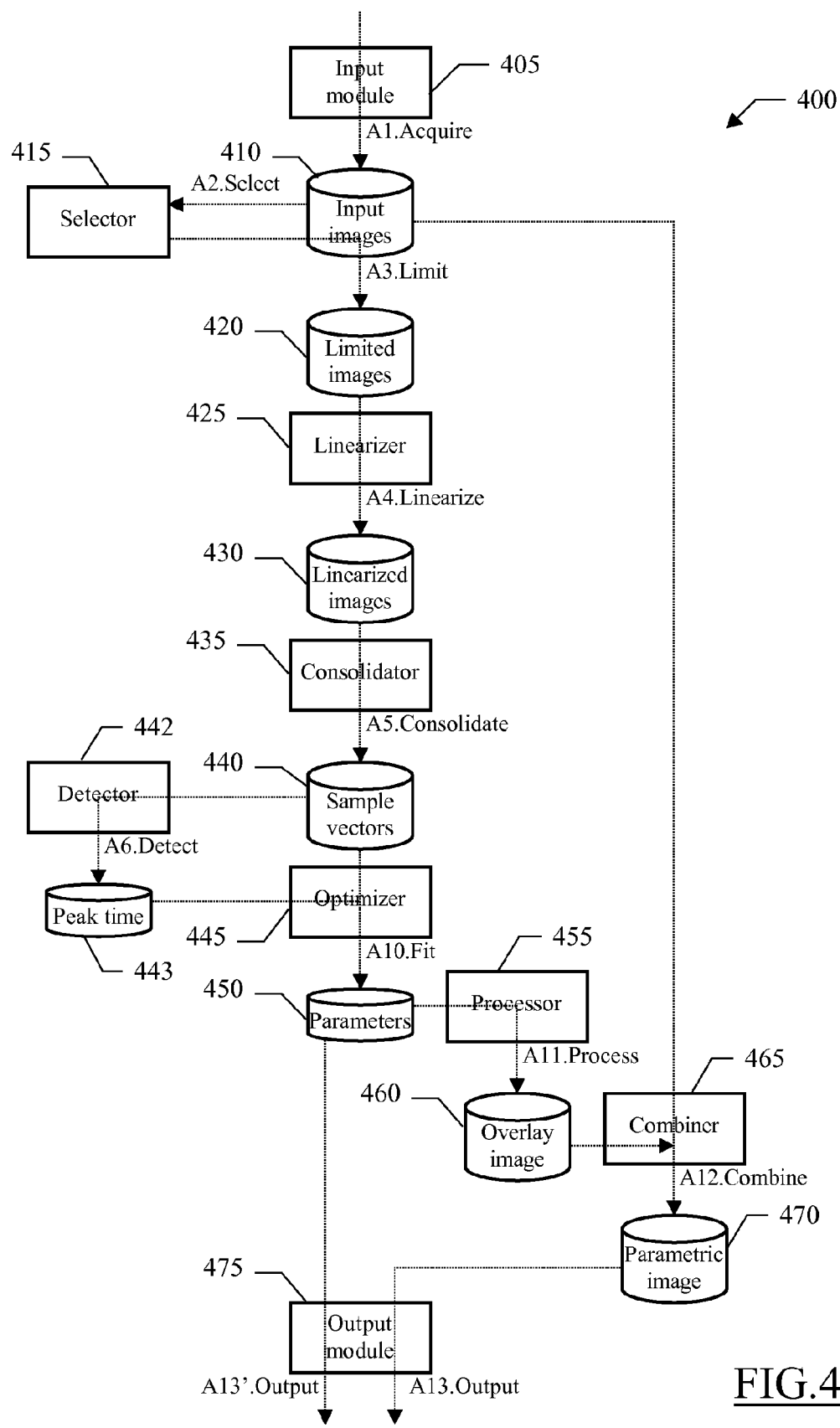
FIG. 4A-4C are collaboration diagrams representing the roles of the main components that may be used to implement a solution according to different embodiments of the invention.

With reference now to FIG. 4A, the main software and/or hardware components that may be used to implement the above-described solution—in the embodiment of the invention based on a single optimization step—are denoted as a whole with the reference 400. The information (programs and data) is typically stored on the hard-disk of the ultrasound scanner and loaded (at least partially) into its working memory when the programs are running, together with an operating system and other application programs (not shown in the figure). The programs are initially installed onto the hard disk from CD-ROM. Particularly, the figure describes the static structure of the system (by means of the corresponding components) and its dynamic behavior (by means of a series of exchanged messages, each one representing a corresponding action, denoted with sequence numbers preceded by the symbol "A").

More specifically, an input module 405 is used to acquire a series of digital images representing the evolution of the body part during the perfusion process. For this purpose, the input module 405 includes a drive that controls the imaging probe (not shown in the figure). For example, the imaging probe drive is provided with a transmit beam former and pulsers for generating the ultrasound pulses to be applied to the body part under analysis; the imaging probe then measures the (analog RF) echo signal that is reflected by each portion of the body part as it is scanned during the perfusion process. The RF analog echo signal is supplied to a receive processor, which pre-amplifies the analog RF echo signal and applies a preliminary time-gain compensation (TGC); the analog RF echo signal is then converted into digital values by an Analog-to-Digital Converter (ADC), and combined into a focused beam signal through a receive beam former. The digital signal so obtained may be processed through further digital algorithms and other linear or non-linear signal conditioners (for example, a post-beam-forming TGC). Particularly, the receive processor may apply a contrast-specific algorithm to substantially remove the dominant (linear) contribution of tissue in the echo signal, with respect to the (non-linear) contribution of the contrast agent; examples of contrast-specific imaging modes include harmonic imaging (HI), pulse inversion (PI), power modulation (PM) and contrast pulse sequencing (CPS) techniques. The digital signal may then be demodulated, log-compressed (so as to obtain a well-balanced video contrast), and scan-converted into a video format. This process results in the recording of a sequence of input images. Each input image is defined by a bitmap consisting of a matrix of values (for example, with M=512 rows and N=512 columns) for respective visualizing elements, i.e., basic picture elements (pixels) or basic volume elements (voxels); each pixel (or voxel) corresponds to a portion of the body part, with its value that represents the intensity of the echo signal that is recorded for that portion of the body part. The sequence of input images so obtained is stored into a corresponding repository 410—hereinafter, the different memory structures and their content will be denoted with the same references for the sake of simplicity (action "A1.Acquire").

A selector 415 may be used by an operator to delimit a portion of the input images 410 (for example, by drawing a corresponding line around one of them with the help of the trackball); this portion represents a region of interest (ROI of the body part on which the desired analysis is to be applied. The operation generates a limitation mask, which consists of a matrix of binary values with the same size as the input images 410; all binary values inside the region of interest are assigned the logic value 1, whereas the binary values outside the region of interest are assigned the logic value 0 (action "A2.Select"). Each input image 410 is then multiplied by the limitation mask pixel-by-pixel, so as to obtain a corresponding sequence of limited images (only including information relating to the region of interest). Particularly, each limited image includes the pixel values of the corresponding input image for the pixels inside the region of interest (as defined by the limitation mask), while the other pixel values are reset to 0. The resulting sequence of limited images is stored into another repository 420 (action "A3.Limit").

A linearizer 425 processes the limited images 420, so as to make each pixel value thereof directly proportional to the corresponding local concentration of the contrast agent; for example, this result may be achieved by applying an inverse log-compression and then squaring the value so obtained (for example, as described in WO-A-2004/110279, the entire disclosures of which is herein incorporated by reference). A sequence of corresponding linearized images so obtained is stored into a further repository 430 (action "A4.Linearize").

The linearized images 430 may be supplied to a consolidator 435, which generates one or more corresponding sample vectors, each one formed by a corresponding sequence of sample values. Particularly, in a configuration of the ultrasound scanner, all the pixels values of each linearized image are combined into a single sample value, which represents the echo signal of the whole region of interest at the corresponding instant; for example, the sample value is calculated as the average of the pixel values different from zero in the linearized image; a median filter may also be applied to the resulting sample vector, so as to reduce the negative effect of any noise. In another configuration of the ultrasound scanner, the linearized images directly define a sample vector for each pixel of the region of interest (consisting of the sequence of corresponding pixel values—not all zero—along the linearized images 430, possibly filtered as indicated above). Alternatively, the linearized images 435 may also be previously sub-sampled (for example, according to a sub-sampling factor set to twice a spatial frequency cutoff that can be chosen as the highest frequency component containing significant energy in one of the linearized images—typically, 2 to 6 pixels); in this case, a sample vector is obtained for each sequence of pixel values of these sub-sampled images (representing a corresponding group of pixels of the region of interest). In any case, the resulting (single or multiple) sample vectors are stored into a repository 440 (action "A5.Consolidate").

Optionally, when the model function P(t) is defined according to equation (15), a detector 442 determines the time to peak of the echo signal corresponding to each sample vector 440; for example, this result may be achieved by fitting the sample vector 440 with a standard model function (e.g., based on a log normal distribution function), and then calculating when it reaches the maximum value (so as to filter out any noise in the echo signal). The time to peak so obtained is stored into a variable 443 (action "A6. Detect").

In any case, an optimizer 445 now determines the model function P(t) that fits each sample vector 440, by exploiting the time to peak 443 when the model function P(t) is defined according to the equation (15). The corresponding parameters (A, m, s, α and Δ in the example at issue) are stored into a table 450 (action "A10.Fit"). Particularly, when a single sample vector is provided the table 450 stores a single set of parameters for the whole region of interest; conversely, when multiple sample vectors are provided the table 450 stores a parameter matrix—with a cell for each pixel value of the (possibly sub-sampled) linearized images 430; each cell of the parameter matrix 450 contains a set of parameters for the corresponding pixel (or group of pixels) of the region of interest.

When the ultrasound scanner is configured to analyze the region of interest at the level of its pixels (or group of pixels), the parameter matrix 450 may be supplied to a processor 455. The processor 455 generates an overlay image, which includes a selected kinetics indicator (for example, the product of the immobilization parameter α by the mean transit time τ) for each cell of the parameter matrix 450. The processor 455 optionally converts the kinetics indicator of each cell into a corresponding discrete value (for example, consisting of 64 or 128 levels that are uniformly distributed between the lowest value and the highest value of all the cells), by possibly applying a gain factor. In this case, the processor 455 may also access a color lookup table (not shown in the figure), which associates all the possible levels with the representation of corresponding colors (that are preferably brighter as the levels increase); for example, each color is defined by an index for accessing a location within a palette containing its actual specification. The kinetics indicator is then replaced with the corresponding color representation. Moreover, when the linearized images 430 were sub-sampled (so that each cell corresponds to a group of pixels of the input images 410), the processor 455 also restores the full-size of the overlay image corresponding to the size of the input images 410 (i.e., M×N pixel values) by means of interpolation techniques (for example, based on the nearest neighbor, bilinear, or bicubic technique). For this purpose, the value of each cell in the overlay image is replicated for the corresponding group of pixels (nearest neighbor interpolation method) and optionally filtered spatially (for example, using a low-pass 2D or 3D spatial filter). The overlay image so obtained is stored into a corresponding file 460 (action "A11.Process").

A combiner 465 may add the overlay image 460 on a selected one of the input images 410. For this purpose, an overlay mask is generated from the original overlay image (i.e., storing the actual value of the kinetics indicator in each cell) by assigning (to each cell) the logic value 1 if its value is strictly higher than a predefined threshold or the logic value 0 otherwise (for example, with the threshold ranging from 0 to 5% of the maximum allowable value). As above, the overlay mask is restored to the full-size of the input images 410 if necessary (i.e., when the linearized images 430 were sub-sampled). An inverted overlay mask is then generated from the overlay mask (by exchanging the logic values 0 and 1). At this point, the combiner 465 generates a masked overlay image by multiplying the overlay image 460 by the overlay mask pixel-by-pixel (so at to maintain the representation of the kinetics indicators that are higher than the threshold value, while the other pixel values are reset to 0); at the same time, the combiner 465 generates a masked input image by multiplying the selected input image (extracted from the repository 410) by the inverted overlay mask pixel-by-pixel (so at to maintain the pixel values of the selected input image that are not included in the masked overlay image, while the other pixel values are reset to 0). The combiner 465 then adds the masked overlay image and the masked input image pixel-by-pixel, so as to obtain a parametric image that is stored into a corresponding file 470 (action "A12.Combine"). In this way, the corresponding kinetics indicator of the overlay image overrides each pixel value of the selected input image only if it has a significant value (i.e., higher than the threshold value). The parametric image 470 is then supplied to an output module 475, which provides it to the operator—for example, causing its displaying (action "A13.Output").

Conversely, when the ultrasound scanner is configured to analyze the region of interest as a whole, the corresponding single set of parameters 450 is directly supplied to the output module 475 for its displaying (action "A13'.Output").

Figure 4B:
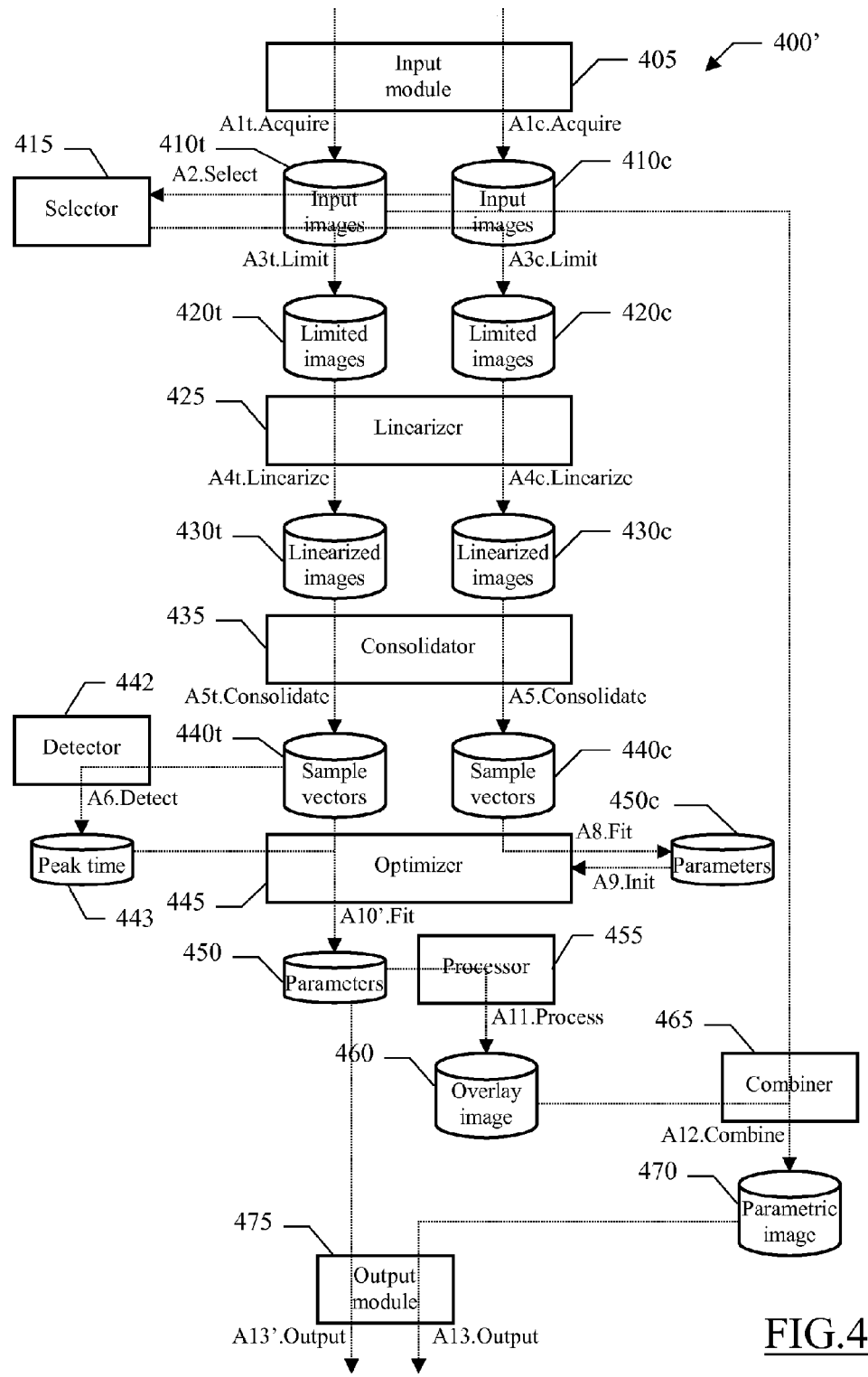

Moving to FIG. 4B, the main software and/or hardware components that may be used to implement an embodiment of the invention implementing two optimization steps based on a double administration of the contrast agent are denoted as a whole with the reference 400' (in the following, the elements corresponding to the ones shown in the preceding figures are indicated with the same references, and their explanation is omitted for the sake of exposition brevity).

In this case, the input module 405 acquires a series of targeted input images 410t for the administration of the targeted contrast agent (action "A1t.Acquire"), and another series of control input images 410c for the administration of the control contrast agent, either beforehand or afterwards (action "A1c.Acquire").

As above, the selector 415 multiplies each targeted input image 410t by the limitation mask, so as to obtain a corresponding sequence of targeted limited images 420t (action "A3t.Limit"); likewise, the selector 415 multiplies each control input image 410c by the same limitation mask, so as to obtain a corresponding sequence of control limited images 420c (action "A3c.Limit"). The linearizer 425 then processes the targeted limited images 420t to obtain a sequence of corresponding targeted linearized images 430t (action "A4t.Linearize"), and the control limited images 420c to obtain a sequence of corresponding control linearized images 430c (action "A4c.Linearize"). Moreover, the consolidator 435 generates one or more targeted sample vectors 440t from the targeted linearized images 430t (action "A5t.Consolidate"), and a same number of control sample vectors 440c from the control linearized images 430c (action "A5c.Consolidate").

At this point, the optimizer 445 determines a control parameter matrix 450c; for each control sample vector 440c, the control parameter matrix 450c stores a set of parameters of the circulation function c(t) that fits it—for example, the parameters A, m and s for the circulation function c(t) of equation (7)—(action "A8.Fit"). Each set of parameters in the control parameter matrix 450c is used to initialize and constraint the same parameters of the model function P(t) for the corresponding targeted sample vector 440t (action "A9.Init"). The optimizer 445 then determines a target parameter matrix 450t (possibly exploiting the time to peak 443); for each targeted sample vector 440t, the target parameter matrix 450t stores a set of parameters of the model function P(t) that fits it (action "A10'.Fit"). The target parameter matrix 450t is then used exactly as above to overlay the selected input image or to display it directly (same actions "A11-A13,A13").

Figure 4C:
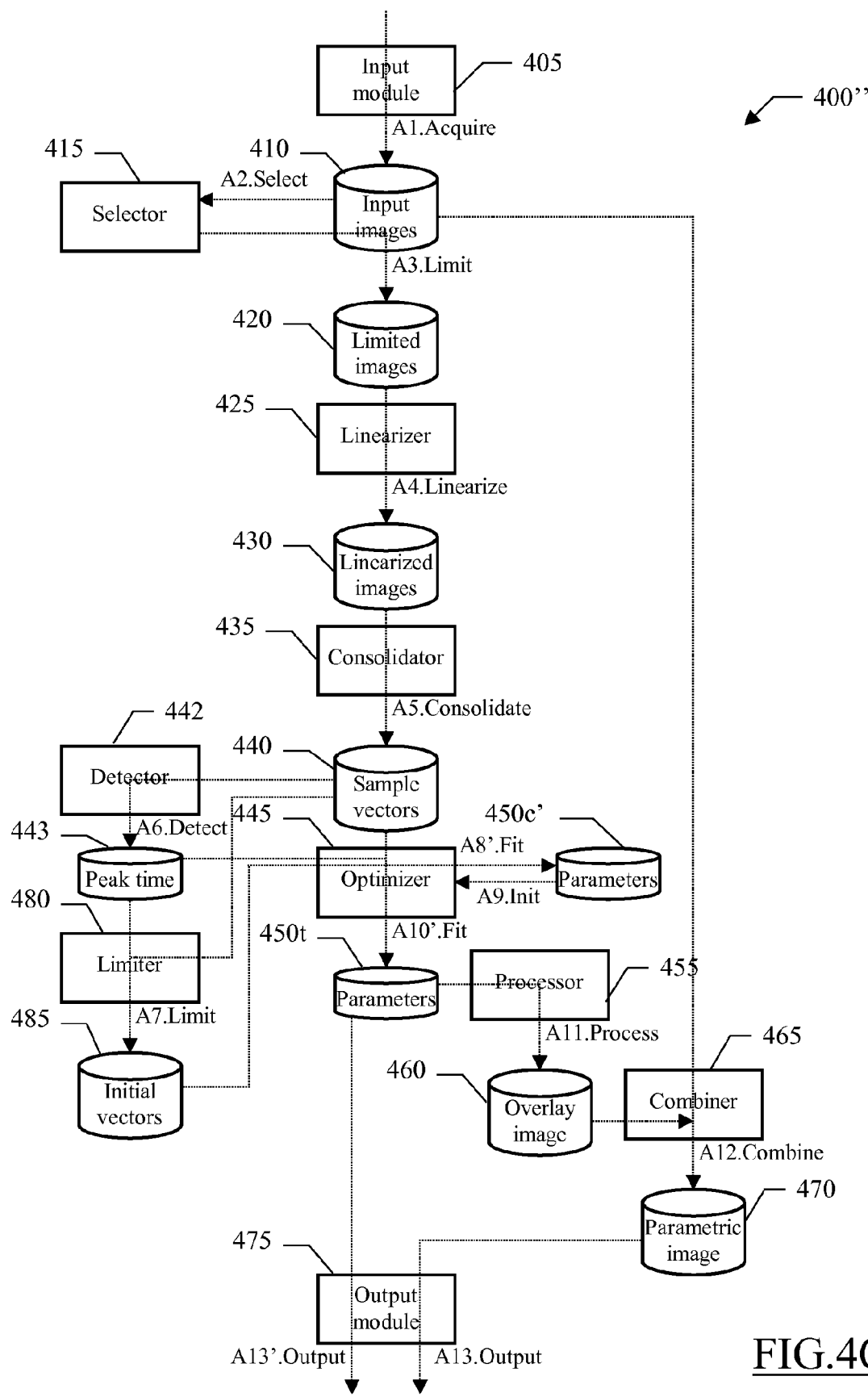

As shown in FIG. 4C, the main software and/or hardware components that may be used to implement an embodiment of the invention implementing two optimization steps based on a single administration of the contrast agent are instead denoted as a whole with the reference 400".

In this case, the sample vectors 440 and the time to peak 443 are obtained as described with reference to FIG. 4A (same actions "A1-A6"). A limiter 480 extracts an initial vector from each sample vector 440; the initial vector includes a subset of its first sample values, which defines the corresponding initial portion of the echo signal according to the time to peak 443. The initial vectors so obtained are stored into a corresponding repository 485 (action "A7.Limit").

At this point, the optimizer 445 determines a similar control parameter matrix 450c'; for each initial vector 485, the control parameter matrix 450c' stores a set of parameters of the circulation function c(t) that fits it—for example, the parameters A, m and s for the circulation function c(t) of equation (7)—(action "A8'.Fit"). The process then continues exactly as above, wherein each set of parameters in the control parameter matrix 440c is used to initialize and constrain the same parameters of the model function P(t) for the corresponding targeted sample vector 440t (action "A9.Init"). The optimizer 445 may then determine the target parameter matrix 450t, which is again used to overlay the selected input image or to display it directly (same actions "A10',A11-A13, A13").

Figure 5A:
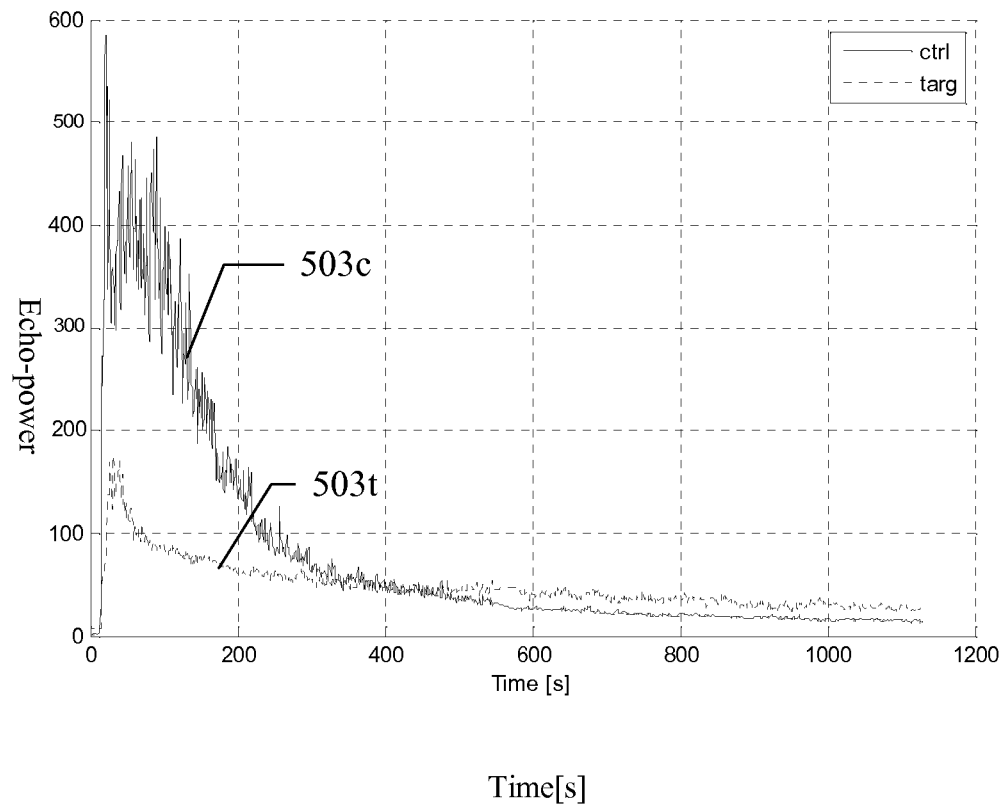
FIG. 5A illustrates experimental echo signals recorded in-vivo.

Moving to FIG. 5A, experimental echo signals being recorded in-vivo are illustrated in a diagram that plots the values of the echo-power signal that was recorded over time according to an embodiment. For this purpose, mice were implanted with murine mammary adenocarcinoma tumor cells of type DA-3, allowed to grow for 7 days (the experiments were conducted in compliance to the directives and with authorizations of the local veterinary authorities). A targeted contrast agent designed with anti-NRP1 (neuropilin-1) antibodies attached on the microbubble surface was administered in two successive intravenous injections. An echo signal was recorded following a first administration of the (targeted) contrast agent, over about 18 minutes. Particularly, a sequence of images in contrast-specific imaging mode were acquired (for example, with Contrast Pulse Sequencing, Siemens Medical Systems) and then linearized. The first administration was followed by administration of free antibodies, at a dose sufficient to saturate all possible receptor sites in the tumor and elsewhere in the organism. An echo signal was then recorded following a second administration of the same (control) contrast agent, again over about 18 minutes. In this case, however, microbubble attachment in the tumor was strongly inhibited by the free antibodies, so that the contrast agent was substantially free to circulate. The same operations were repeated on different mice. An example of the evolution over time of the echo signal for the targeted contrast agent within a region of interest encompassing the DA-3 tumor area (for a mouse representative of any similar mice) is denoted in the figure with 503t; the same evolution over time of the echo signal for the control contrast agent is instead denoted with 503c. As can be seen, the echo signal 503c is far higher than the echo signal 503t (since a large fraction of the targeted contrast agent immobilized elsewhere in this case); moreover, the decrease of the echo signal 503c (after reaching its peak) is far slower than the one of the echo signal 503t (because of the contribution of the targeted contrast agent that remained immobilized).

Figure 5C:
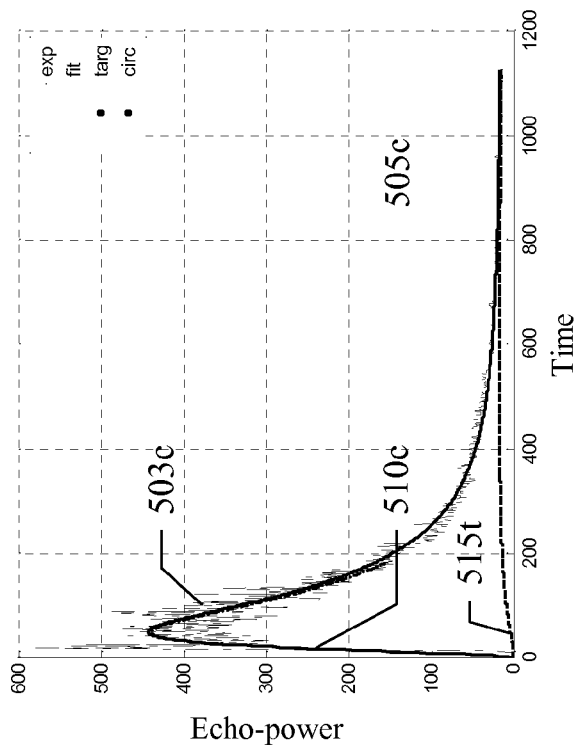
FIGS. 5B-5C shows an exemplary application of a solution according to an embodiment of the invention to these experimental echo signals.
Figure 5B:
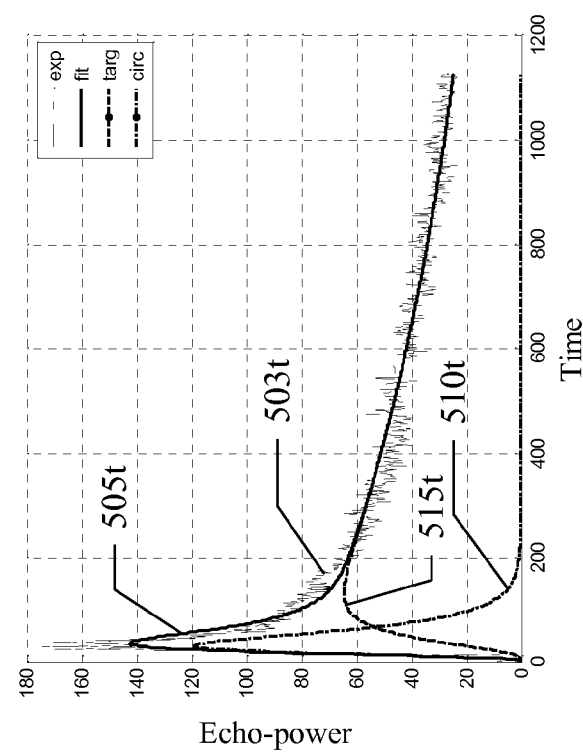

With reference now to FIG. 5B, the echo signal 503t of the targeted contrast agent was fitted by the model function P(t) according to an embodiment of the invention—as defined in equation (8); the instance of the model function P(t) so determined in represented in the figure with a curve 505t—given by the sum of the corresponding circulation function and dynamic immobilization function (represented in the figure with a curve 510t and a curve 515t, respectively). Particularly, in this case the values of the parameters of the model function P(t) were A=6,774, m=3.84, s=0.577, $\alpha=1.07 \cdot 10^{-2}$ s$^{-1}$ and $\Delta$=998 s.

Considering instead FIG. 5C, the echo signal 503c of the control contrast agent was fitted by the same model function P(t) of equation (8); the instance of the model function P(t) so determined in represented in the figure with a curve 505c—given by the sum of the corresponding circulation function and dynamic immobilization function (represented in the figure with a curve 510c and a curve 515c, respectively). Particularly, in this case the values of the parameters of the model function P(t) were A=74,140, m=4.72, s=0.893, $\alpha=0.02 \cdot 10^{-2}$ $s^{-1}$ and $\Delta$=4,813 s.

As may be noted, the immobilization parameters $\alpha$ and the decay parameters $\Delta$ are remarkably different for the targeted contrast agent and the control contrast agent. Particularly, the immobilization parameter $\alpha$ for the targeted contrast agent ($\alpha=1.07 \cdot 10^{-2}$ $s^{-1}$) is significantly higher than the immobilization parameter $\alpha$ for the control contrast agent ($\alpha=0.02 \cdot 10^{-2}$ $s^{-1}$), reflecting the far higher affinity of the targeted contrast agent for its receptors.

Figure 6B:
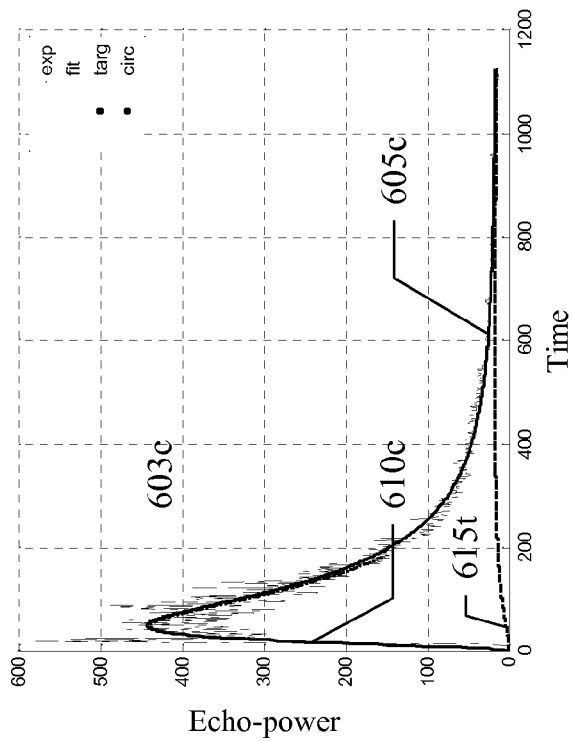
FIGS. 6A-6B shows another exemplary application of a solution according to an embodiment of the invention.
Figure 6A:
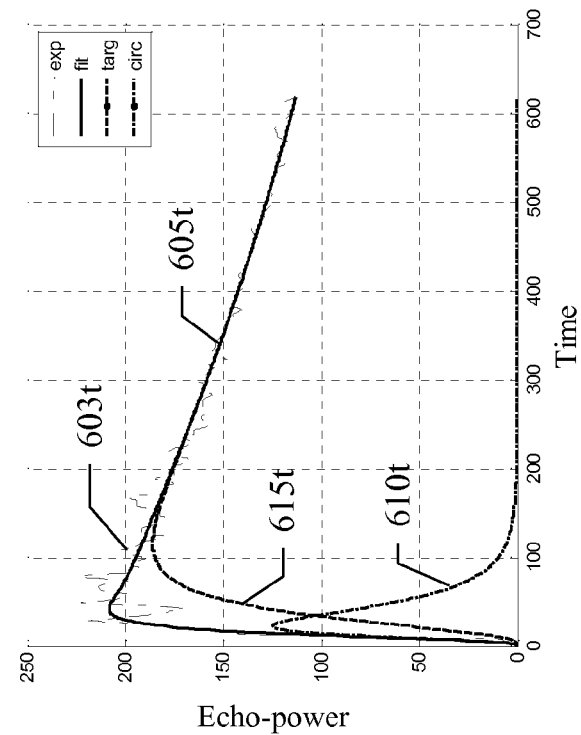

Another exemplary application of the same embodiment to an inflammatory scenario is illustrated in FIGS. 6A-6B. In this case, P-Selectin expression was imaged in twenty OF1 mice of 6-10 weeks of age, in which inflammation was induced by a 30 μL injection of TNF-α in the hind limb (recombinant mouse TNF-α, 0.017 μg/μL, Calbiochem). After 24 h, the muscle was imaged over time for approximately 600 s.

With reference in particular to FIG. 6A, an echo signal—denoted with 603t—was recorded following an administration of a targeted contrast agent designed to bind specifically the P-Selectin receptors. The echo signal 603t of the targeted contrast agent was again fitted by the model function P(t) of equation (8), represented in the figure with a curve 605t—given by the sum of the corresponding circulation function and dynamic immobilization function (represented in the figure with a curve 610t and a curve 615t, respectively). Particularly, in this case the values of the parameters of the model function P(t) were A=5,879, m=3.60, s=0.632, $\alpha=3.54 \cdot 10^{-2}$ $s^{-1}$ and $\Delta$=943 s.

Moving to FIG. 6B, an echo signal—denoted with 603c—was instead recorded following an administration of a control contrast agent with no specificity to the P-Selectin receptors according to an embodiment. The echo signal 603c of the control contrast agent was fitted by the same model function P(t) of equation (8); the instance of the model function P(t) so determined in represented in the figure with a curve 605c—given by the sum of the corresponding circulation function and dynamic immobilization function (represented in the figure with a curve 610c and a curve 615c, respectively). Particularly, in this case the values of the parameters of the model function P(t) were A=23,293, m=4.92, s=0.927, $\alpha=0$ $s^{-1}$ and $\Delta$=180 s.

As may be noted, the immobilization parameters $\alpha$ and the decay parameters $\Delta$ for the targeted contrast agent and the control contrast agent are even more different (i.e., $\alpha=3.54 \cdot 10^{-2}$ $s^{-1}$ and $\Delta$=943 s for the targeted contrast agent against $\alpha=0$ $s^{-1}$ and $\Delta$=180 s for the control contrast agent).

In order to illustrate the improvement of a proposed embodiment with respect to the prior art, the echo signal shown in FIG. 5A was fitted by the model function known in the art that does not take into account the decay of the echo signal from the immobilized contrast agent ($\Delta \to \infty$).

Figure 7B:
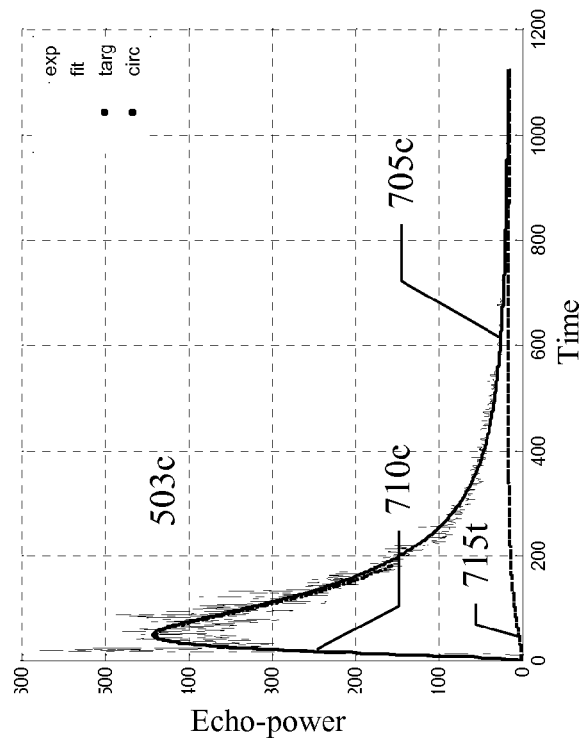
FIGS. 7A-7B, 8A-8B show comparison examples obtained by applying a technique known in the art to the same experimental echo signals.
Figure 7A:
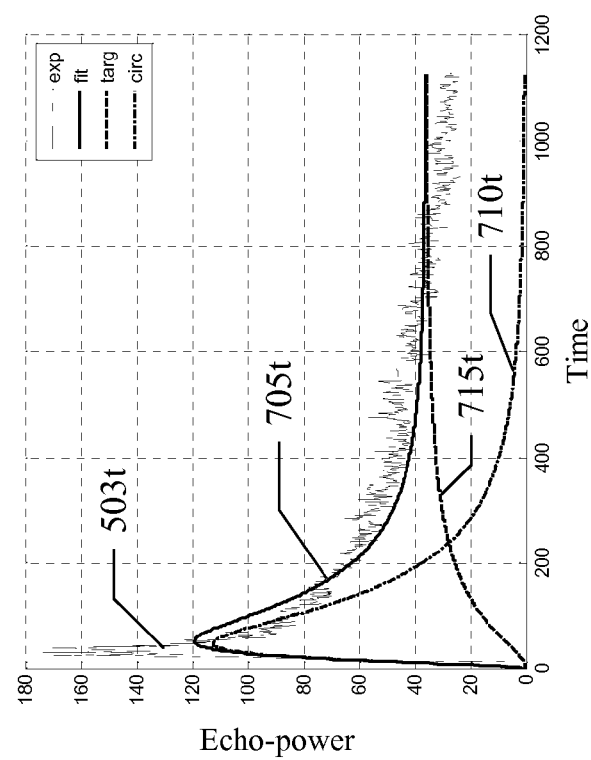

With reference in particular to FIG. 7A, the above-described echo signal 503t of the targeted contrast agent was fitted by the model function of equation (12); the instance of the model function so determined is represented in the figure with a curve 705t—given by the sum of the corresponding circulation function and permanent immobilization function (represented in the figure with a curve 710t and a curve 715t, respectively). Particularly, in this case the values of the parameters of the model function were A=20,575, m=4.79, s=0.941 and $\alpha=0.17 \cdot 10^{-2}$ $s^{-1}$. As may be noted, the quality of the obtained result is significantly degraded; particularly, the immobilization parameter $\alpha$ for the targeted contrast agent ($\alpha=0.17 \cdot 10^{-2}$ $s^{-1}$) is significantly lower than the one provided by the proposed solution (i.e., $\alpha=1.17 \cdot 10^{-2}$ $s^{-1}$).

Considering instead FIG. 7B, the above-described echo signal 503c of the control contrast agent was fitted by the same model function of equation (12); the instance of the model function so determined is represented in the figure with a curve 705c—given by the sum of the corresponding circulation function and permanent immobilization function (represented in the figure with a curve 710c and a curve 715c, respectively). Particularly, in this case the values of the parameters of the model function were A=74,966, m=4.73, s=0.899 and $\alpha=0.02 \cdot 10^{-2}$ $s^{-1}$. The obtained result is now substantially the same as above, since the control contrast agent does not experience any significant decay of the echo signal from the immobilized contrast agent (its immobilization being negligible).

Figure 8B:
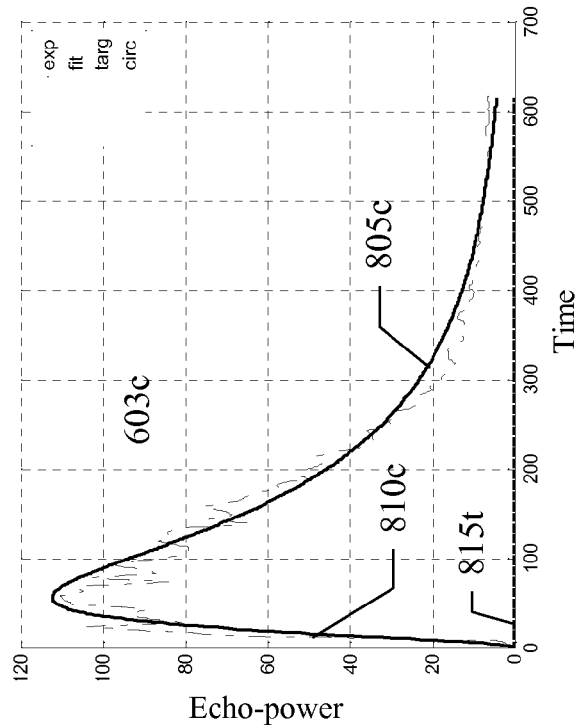
Figure 8A:
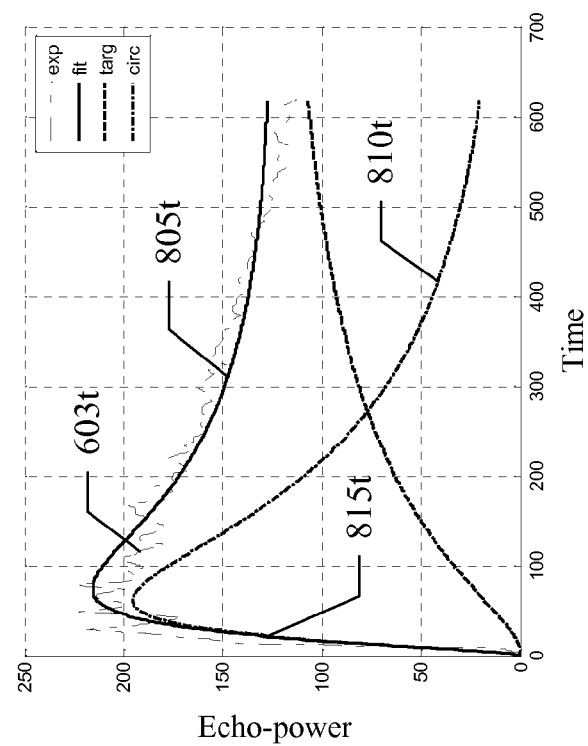

Likewise, with reference to FIG. 8A, the above-described echo signal 603t of the targeted contrast agent was again fitted by the model function of equation (12); the instance of the model function so determined is represented in the figure with a curve 805t—given by the sum of the corresponding circulation function and permanent immobilization function (represented in the figure with a curve 810t and a curve 815t, respectively). Particularly, in this case the values of the parameters of the model function were A=59,219, m=5.30, s=1.072 and $\alpha=0.21 \cdot 10^{-2}$ $s^{-1}$. In this case as well, the quality of the obtained result is significantly degraded; particularly, the immobilization parameter $\alpha$ for the targeted contrast agent ($\alpha=0.21 \cdot 10^{-2}$ $s^{-1}$) is significantly lower than the one provided by the proposed embodiment (i.e., $\alpha=3.54 \cdot 10^{-2}$ $s^{-1}$).

Considering instead FIG. 8B, the above-described echo signal 603c of the control contrast agent was fitted by the same model function of equation (12); the instance of the model function so determined is represented in the figure with a curve 805c—given by the sum of the corresponding circulation function and permanent immobilization function (represented in the figure with a curve 810c and a curve 815c, respectively). Particularly, in this case the values of the parameters of the model function were A=23,293, m=4.92, s=0.927 and $\alpha=0$ $s^{-1}$. The obtained result is again substantially the same as above, since the control contrast agent does not immobilize in a significant way, and thus its echo signal cannot experience any meaningful decay.

MODIFICATIONS

Naturally, in order to satisfy local and specific requirements, a person skilled in the art may apply to the solution described above many logical and/or physical modifications and alterations. More specifically, although the present disclosure has been described with a certain degree of particularity with reference to embodiment(s) thereof, it should be understood that various omissions, substitutions and changes in the form and details as well as other embodiments are possible. Particularly, an embodiment of the proposed solution may even be practiced without the specific details (for example, the numerical examples) set forth in the preceding description to provide a more thorough understanding thereof; conversely, well-known features may have been omitted or simplified in order not to obscure the description with unnecessary particulars. Moreover, it is expressly intended that specific elements and/or method steps described in connection with any disclosed embodiment of the invention may be incorporated in any other embodiment as a matter of general design choice.

Particularly, similar considerations apply if the ultrasound scanner has a different structure or includes other units (for example, with an imaging probe of the linear-, convex-, phased-, or matrix-array type). Alternatively, an embodiment is applied in a medical imaging system that consists of an ultrasound scanner and a distinct computer (or any equivalent data processing system); in this case, the measured data is transferred from the ultrasound scanner to the computer for its processing (for example, through a removable disk, a memory key, or a network connection). In any case, the application to any other medical imaging system—for example, based on Magnetic Resonance Imaging (MRI) or X-ray Computed Tomography (CT)—is within the scope of the disclosure.

An embodiment lends itself to be put into practice with equivalent target-specific contrast agents for whatever (biological) target; for example, the contrast agent may be specific for enhancing Magnetic Resonance imaging or X-ray Computed Tomography imaging. However, the application of an embodiment to a non target-specific contrast agent—for example, for detecting the slowly-moving contrast agent only—or even to a mixture of target-specific contrast agent and non target-specific contrast agent is not excluded.

Similar considerations apply if the echo signal is recorded in any other way (for example, by applying a motion compensation on the input images, without any linearization when the pixel values are already proportional to the concentration of the contrast agent, by taking into account the whole input images without selecting any region of interest, and the like), or if the echo signal is fitted by the model function with equivalent optimization techniques (for example, based on neural networks).

Alternatively, the contrast agent may also be administered with a continuous infusion, with or without the application of destructive frames, orally (for example, for imaging the gastro-intestinal tract), via a nebulizer into the airways, and the like.

Nothing prevents combining the circulation function, the permanent immobilization function and the decay function in any other way (for example, with a weighted sum).

The definition of different permanent immobilization functions (for example, based on a non-linear immobilization rate) is not excluded.

Any other kinetics indicators may be calculated from the parameters of the model function. For example, it is possible to determine the maximum or the minimum of the immobilization rate, any other combination of the two decay parameters $\Delta_1$ and $\Delta_2$ when the decay function is of the bi-exponential type—for example, the maximum or the minimum between $B \cdot \Delta_1$ and $(1-B) \cdot \Delta_2$, the maximum or the minimum between B and (1−B)—and the like.

Likewise, the circulation function may be combined in any other way with the decay function in the simplified definition of the model function (for example, $A \cdot \Delta_1$, $A \cdot \Delta_2$, the maximum or the minimum between $A \cdot \Delta_1$ and $A \cdot \Delta_2$, and the like).

Alternatively, it may be possible to set the time offset of the decay function to a predefined multiple of the time to peak (for example, 1.5-2 times), or even to a fixed value (for example, 20-30 s).

Similar considerations apply if the decay function is defined by an exponential function with three or more time constants.

In any case, the modeling of the decay of the echo signal from the immobilized contrast agent with other functions (for example, based on a hyperbolic or squared law) is contemplated.

Likewise, alternative circulation functions are tenable. For example, when the contrast agent re-circulates in the body part, the circulation function may be expressed as the sum of multiple elementary circulation functions with decreasing amplitude (representing the successive passages of the contrast agent). In any case, nothing prevents modeling the circulation of the contrast agent with different circulation functions (such as the γ-variate function, the local density random walk function, or any linear combination thereof or with the log normal distribution function).

The initial portion of the echo signal (to be used in the first optimization step of an embodiment of the invention based on the single administration of the contrast agent) may also be set to a predefined percentage of the time to peak (for example, 90-80%), or even to a fixed value (for example, 20-30 s).

It may also be possible to select different weights for the initial portion and the remaining portion of the echo signal during the second optimization step. However, the use of the same weights for the whole extension of the echo signal is not excluded.

The result of the first optimization step (in an embodiment of the invention based on either the double administration or the single administration of the contrast agent) may be used to constrain the corresponding parameters of the model function in any other way; for example, in a simplified implementation it may be possible to maintain them simply constant during the second optimization step.

Moreover, an embodiment lends itself to be implemented with an equivalent method (by using similar steps, removing some steps being non-essential, or adding further optional steps); moreover, the steps may be performed in a different order, concurrently or in an interleaved way (at least in part).

Similar considerations apply if the program (which may be used to implement an embodiment of the invention) is structured in a different way, or if additional modules or functions are provided; likewise, the memory structures may be of other types, or may be replaced with equivalent entities (not necessarily consisting of physical storage media). In any case, the program may take any form suitable to be used by any data processing system or in connection therewith (for example, within a virtual machine); particularly, the program may be in the form of external or resident software, firmware, or microcode (either in object code or in source code—for example, to be compiled or interpreted).

Moreover, it may be possible to provide the program on any tangible computer-usable medium; the medium can be any element suitable to contain, store, communicate, propagate, or transfer the program. For example, the medium may be of the electronic, magnetic, optical, electromagnetic, infrared, or semiconductor type; examples of such medium are fixed disks (where the program may be pre-loaded), removable disks, tapes, cards, wires, fibers, wireless connections, networks, broadcast waves, and the like. In any case, an embodiment of the present invention lends itself to be implemented even with a hardware structure (for example, integrated in a chip of semiconductor material), or with a combination of software and hardware.

From the foregoing it will be appreciated that, although specific embodiments have been described herein for purposes of illustration, various modifications may be made without deviating from the spirit and scope of the disclosure. Furthermore, where an alternative is disclosed for a particular

The invention claimed is:

1. A system for analyzing a body part of a patient being perfused with a contrast agent capable of circulating within the patient and of being immobilized on a biological target, wherein the system includes:
a module operable to provide a representation of an echo signal that is indicative of a response over time to an interrogation signal of the body part,
an electronic circuit operable, or configurable with software, firmware, or microcode, to fit the echo signal by a time model function that models an evolution over time of the echo signal, the time model function including a combination of a time circulation function that models a contribution over time of the circulation of the contrast agent to the echo signal, an immobilization function that represents the immobilization of the contrast agent, and a time decay function that models a decay over time of the echo signal from the immobilized contrast agent, and
the electronic circuit operable, or configurable with software, firmware, or microcode, to estimate at least one kinetics indicator of the contrast agent from the time model function.

2. The system according to claim 1, wherein the time circulation function models the circulation of the contrast agent being administered as a bolus.

3. The system according to claim 1, wherein the immobilization function is a time immobilization function that models the immobilization of the contrast agent over time.

4. The system according to claim 3, wherein the time model function includes a sum of the time circulation function with a product of an immobilization parameter that represents a constant immobilization rate of the contrast agent by a convolution product between the time circulation function and the time decay function.

5. The system according to claim 4, wherein the electronic circuit is further operable, or configurable with software, firmware, or microcode, to estimate a mean transit time of the circulation of the contrast agent from the time circulation function and to calculate an immobilization indicator by multiplying the mean transit time by the immobilization parameter, the immobilization indicator representing a percentage of immobilization of the contrast agent.

6. The system according to claim 1, wherein for each instant until a time offset the time model function corresponds to the time circulation function, and for each further instant after the time offset the time model function includes a product between a value of the time circulation function at the time offset by the time decay function referred to the time offset.

7. The system according to claim 6, wherein the electronic circuit is further operable, or configurable with software, firmware, or microcode, to set the time offset according to the reaching of an absolute peak value by the echo signal.

8. The system according to claim 1, wherein the time decay function is an exponential function based on a decay parameter that represents a time constant of the decay of the echo signal from the immobilized contrast agent.

9. The system according to claim 1, wherein the time decay function is a weighted sum of a plurality of exponential functions each one based on a corresponding decay parameter that represents a time constant of the decay of the echo signal from a corresponding category of the immobilized contrast agent.

10. The system according to claim 1, wherein the time circulation function is based on a log normal distribution function.

11. The system according to claim 1 wherein:
the module is operable to provide a representation of a further echo signal that is indicative of a response over time to the interrogation signal of the body part being perfused with a further contrast agent that is capable of circulating within the patient without immobilizing,
the electronic circuit is operable, or configurable with software, firmware, or microcode, to further fit the further echo signal with a further time circulation function that models the circulation of the further contrast agent,
the electronic circuit is further operable, or configurable with software, firmware, or microcode, to constrain the time circulation function according to the further time circulation function.

12. The system according to claim 1 wherein:
the electronic circuit is operable, or configurable with software, firmware, or microcode, to further fit an initial portion of the echo signal with a further time circulation function that models the circulation of the contrast agent, and
the electronic circuit is further operable, or configurable with software, firmware, or microcode, to constrain the time circulation function according to the further time circulation function.

13. The system according to claim 12, wherein the electronic circuit is further operable, or configurable with software, firmware, or microcode, to select the initial portion according to the reaching of an absolute peak value by the echo signal.

14. The system according to claim 12, wherein the electronic circuit is further operable, or configurable with software, firmware, or microcode, to assign a first weight to the first portion of the echo signal and a second weight that is higher than the first weight to a remaining portion of the echo signal for fitting the time model function.

15. The system according to claim 11, wherein each time circulation function includes a set of circulation parameters, the computing circuit being further operable to constrain each circulation parameter of the time circulation function within a range based on the corresponding circulation parameter of the further time circulation function.

16. A method for analyzing a body part of a patient being perfused with a contrast agent that is capable of circulating within the patient and of being immobilized on a biological target, wherein the method includes the steps of:
providing a representation of an echo signal that is indicative of a response over time to an interrogation signal of the body part,
fitting the echo signal by a time model function that models an evolution over time of the echo signal, the time model function including a combination of a time circulation function that models a contribution over time of the circulation of the contrast agent to the echo signal, an immobilization function that represents the immobilization of the contrast agent, and a time decay function that models a decay over time of the echo signal from the immobilized contrast agent, and
estimating at least one kinetics indicator of the contrast agent from the time model function.

17. The method according to claim 16, wherein the time circulation function models the circulation of the contrast agent being administered as a bolus.

18. The method according to claim 16, wherein the immobilization function is a time immobilization function that models the immobilization of the contrast agent over time.

19. The method according to claim 18, wherein the time model function includes a sum of the time circulation function with a product of an immobilization parameter that represents a constant immobilization rate of the contrast agent by a convolution product between the time circulation function and the time decay function.

20. The method according to claim 19, wherein the step of estimating includes:
estimating a mean transit time of the circulation of the contrast agent from the time circulation function and calculating an immobilization indicator by multiplying the mean transit time by the immobilization parameter, the immobilization indicator representing a percentage of immobilization of the contrast agent.

21. The method according to claim 16, wherein for each instant until a time offset the time model function corresponds to the time circulation function, and for each further instant after the time offset the time model function includes a product between a value of the time circulation function at the time offset by the time decay function referred to the time offset.

22. The method according to claim 21, wherein the step of fitting includes:
setting the time offset according to the reaching of an absolute peak value by the echo signal.

23. The method according to claim 16, wherein the time decay function is an exponential function based on a decay parameter that represents a time constant of the decay of the echo signal from the immobilized contrast agent.

24. The method according to claim 16, wherein the time decay function is a weighted sum of a plurality of exponential functions each one based on a corresponding decay parameter that represents a time constant of the decay of the echo signal from a corresponding category of the immobilized contrast agent.

25. The method according to claim 16, wherein the time circulation function is based on a log normal distribution function.

26. The method according to claim 16, further including the steps of:
providing a representation of a further echo signal that is indicative of a response over time to the interrogation signal of the body part being perfused with a further contrast agent that is capable of circulating within the patient without immobilizing,
further fitting the further echo signal with a further time circulation function that models the circulation of the further contrast agent,
wherein the step of fitting includes:
constraining the time circulation function according to the further time circulation function.

27. The method according to claim 16, further including the step of:
further fitting an initial portion of the echo signal with a further time circulation function that models the circulation of the contrast agent,
wherein the step of fitting includes:
constraining the time circulation function according to the further time circulation function.

28. The method according to claim 27, wherein the step of further fitting includes:
selecting the initial portion according to the reaching of an absolute peak value by the echo signal.

29. The method according to claim 27 wherein the step of fitting includes:
assigning a first weight to the first portion of the echo signal and a second weight higher than the first weight to a remaining portion of the echo signal for fitting the time model function.

30. The method according to claim 26, wherein each time circulation function includes a set of circulation parameters, the step of constraining including:
constraining each circulation parameter of the time circulation function within a range based on the corresponding circulation parameter of the further time circulation function.

31. A computer program for performing the method of claim 16 when the computer program is executed on a data processing system.

32. A computer program product including a computer-usable medium that embodies a computer program, the computer program, when executed on a data processing system, causing the system to perform a method for analyzing a body part of a patient being perfused with a contrast agent that is capable of circulating within the patient and of being immobilized on a biological target, wherein the method includes the steps of:
providing a representation of an echo signal that is indicative of a response over time to an interrogation signal of the body part,
fitting the echo signal by a time model function that models an evolution over time of the echo signal, the time model function including a combination of a time circulation function that models a contribution over time of the circulation of the contrast agent to the echo signal, an immobilization function that represents the immobilization of the contrast agent, and a time decay function that models a decay over time of the echo signal from the immobilized contrast agent, and
estimating at least one kinetics indicator of the contrast agent from the time model function.

33. The system according to claim 1 wherein the module includes a probe.

34. The system according to claim 1 wherein the module includes a memory device that is operable to store the echo signal.

35. The system according to claim 1 wherein the module includes a network connection.

* * * * *